US010184155B2

(12) United States Patent
Khatib

(10) Patent No.: US 10,184,155 B2
(45) Date of Patent: Jan. 22, 2019

(54) GENETIC TESTING FOR IMPROVED CATTLE FERTILITY

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 12 days.

(21) Appl. No.: 15/138,221

(22) Filed: Apr. 26, 2016

(65) Prior Publication Data

US 2016/0237508 A1 Aug. 18, 2016

Related U.S. Application Data

(62) Division of application No. 13/798,176, filed on Mar. 13, 2013.

(60) Provisional application No. 61/621,571, filed on Apr. 8, 2012.

(51) Int. Cl.

*C12Q 1/68* (2018.01)
*C12Q 1/6888* (2018.01)
*A61D 19/02* (2006.01)
*C12Q 1/6876* (2018.01)

(52) U.S. Cl.

CPC ........... *C12Q 1/6888* (2013.01); *A61D 19/02* (2013.01); *C12Q 1/6876* (2013.01); *C12Q 2600/124* (2013.01); *C12Q 2600/156* (2013.01)

(58) Field of Classification Search

None

See application file for complete search history.

(56) References Cited

U.S. PATENT DOCUMENTS

2009/0216074 A1* 8/2009 Khatib ................ C12Q 1/6876 600/35

OTHER PUBLICATIONS

Li et al. (Journal of Dairy Research (2012) 79:310-317; published online Jun. 12, 2012) (Year: 2012).*

DBSNP record having identifier ss428952529 (submitted by Lewinlab, accessed from https://www.ncbi.nlm.nih.gov/projects/SNP/snp_ss.cgi?subsnp_id=428952529 on Aug. 31, 2017, two pages, submitted Jul. 4, 2011) (Year: 2011).*

W. A. Kues, S. Sudheer, D. Herrmann, J. W. Camwath, V. Havlicek, U. Besenfelder, H. Lehrach, J. Adjaye, and H. Niemann. Genome-wide expression profiling reveals distinct clusters of transcriptional regulation during bovine preimplantation development in vivo. PNAS. Dec. 16, 2008. vol. 105. No. 50: 19768-19773.

* cited by examiner

*Primary Examiner* — Juliet C Switzer

(74) *Attorney, Agent, or Firm* — Kening Li; Duane Morris LLP

(57) ABSTRACT

Arrays of nucleic acid molecules, kits, methods of genotyping and marker assisted bovine breeding methods based on novel SNPs on genes of the bovine transforming growth factor-β (TGF-β) signaling pathway for improved bovine fertilization rate. The methods and compositions of the present invention are related to SNPs in the DNA-binding protein inhibitor 3 (ID3) gene, and in the bone morphogenetic protein 4 (BMP4) gene corresponding to position 2702 of SEQ ID NO: 2. Also disclosed are methods for determining viability of developing bovine embryos by measuring the expression level of one or more target genes in the TGF-signaling pathway, and selecting for implantation only embryos whose target gene expression level is not up-regulated.

4 Claims, 4 Drawing Sheets

Specification includes a Sequence Listing.

```
   1  tctgtctatc tccttccttc cagcacttcc caacctcatt gctcagtatg aaggcgctca
61   gcccggttcg cggctgctac gaggcggtat gctgcctgtc ggaacgcagc ctggccatcg
121  cgcggggccg tggcaagagc ccggccgccg aggagccgct gagcctgctt gacgacatga
181  accactgcta ctcgcgactg agggaactgg taccccggagt cccgcgaggc actcagctta
241  gccaggtgga aatcctgcag cgcgtcatcg actacatcct cgacctgcag gtggtcctgg
301  ccgagccggc ccctgggccc ccagacggcc cgcatcttcc catccaggtg cgcgcgggcg
361  tgctcgggag ctggggcggg gctgagctcc agggctggga tgctacgggg accccctggac
421  cttccaaact ccgtgcgtaa acccttcccc cctttttcctt ctctcagaca gctgagctcg
481  ctccggaact tgtgatctcc aacgaccaaa ggagcttctg ccactgacct ggcccgtcct
541  ggcgcctcca ggtgagtatc caagccttct ctcgggggcg gggaaggggg acagctggtg
601  cttaaacggc gatcttggag ttggtaggcc ttttaaagga ttaccgcggc cccctcggtt
661  tagggaaatt caggccagag agacgcaagt gacttgcccg tggtcacagc aaatgaatga
721  cggaaccaat tctgatccag agttcgtttc aaccttaagt gcacgttgtt cccgtcctcc
781  ccattggcca aaggtgcgaa actatagacg caggtccgac tagataaaat aaccagtctg
841  tctgtggctt ggagtcgtaa aaggagccgc gtttttctca gcccccctcc caactagtgt
  FORWARD PRIMER
901  cacttccaat aggcaggggt ggtgcaagct ccgcctgtgg tctttcggcg ccaactgggt
961  gggggcagtg tggggcgcga gttatcagct ggaggtagag accaagtttc ctccctggcg
1021 ccggccagtc tgcggacggc ccccgcttgg gcgcgctcgg cggaaactga cggctccctg
1081 gtcttctttc ctccccccgcc cagaacgcag gtgctggcgc ccgtccggga ccccgggacc
1141 ctctacggcc ggaagcccga gggcatggat gggcctcaac cttgccctgc ccacttgact
1201 tccccaaacc cc[T/C]gcctcga ggctggacct gcgcccggga gcgaaggact gtgaacttgg
1261 gtggcctaaa gagccggcgc tagctctggg caccagctgg gcaacctccc cctgccctca
1321 ccccactccc aagttttaaa gactgtcttt cagtgtgtgg aggtgtacgg ggttgggggt
1381 gggggctggc tgttctccaa attctgcctt ggccaaggca gcggtagagc tggtcttctg
1441 gtctccttgg agaaagactc tgttgccctg attatgaact ctataataga gtatttagct
1501 tttgtacctt ttttgcagga aggtgacttt ctgtaaccat gcgatgtata ttaaactttt
1561 tataaaagtt aacattttgc ataataaacg gtttttaaac acttgtgttt  ataatttgat
  REVERSE PRIMER
1621 tccttaagtg ctaacactgt ttctcacaaa gctggattta gggagaataa  attcatgtct
ttcttggagc  ttaggaaaag
```

Figure 2 Partial Sequence of Bovine ID3 Gene

```
1    aggggctgga agaaaaacag agtccgtctg cgccagtctc attatattca aatattcatt
61   ttaggagcca ttccgtagtg ccatccagag caacgcactg ccgcagctcc tctgagcctt
121  tccagcaagt ttgttcaaga ttggctgtca agaatcatgg actgttatta tatgccttgt
181  tttctgtcag tgagtagaca cctcttcctt ccctcttccc gggaattcac tctgccctcc
241  ccacccgcgc tcgccttgtg tccctcccgt cggaccttcc ttccagagtc cacactcttc
301  tttctggcag cgctgtcgct ttcttctagg ccgggcagcc actgcgctcg gagcctaccg
361  gttctggttg aagtgcagct tgctccactg gctctctgtc tgatcactgc gttacaagaa
421  aggggagcga gaaggggctg aacaaacgga aagtcctcag tcgggggagt tgaccgcccc
481  cctccccaca tgactgggag cacccagtgc ccctgtggcg cgctcctagc tgcttgtcaa
541  aactcacaga ggtcgccctt ggaatcatcc cctcccacac cccttccct gggagtgagc
601  gagagggcgc gatcagatgc tttttgctgg gcatttcaaa actcctcagc cacagtaaaa
661  taaaccctct ggccactcgg tacgctccca gatcctgccg ccccgtgtct tcaccctgct
721  cctgcttctc tgctttccct ccctccgaac cagctggaag ttgtggaagt cgggctagga
781  agggcggagg aagaaggggg gtggaggaga agggagagag aggctgaagg tctgaagtgg
841  agaggagagc gctggcattt gaactctccc tcccccaccc ttctttacct tctcactgtt
901  aactgtttat ccctaaagaa gccaagctga gatcatggct cagatagcag ttgggacaaa
961  aaaagattaa caggatggag gctatctgat ttggggttat ttgactgtaa acaagttaga
1021 ccaagtaatt acagggcaat tcctactttc aggccgtgca tggctgcagc tggtggtggt
1081 ggtggggggg ggtgtgtgtg tcagaggaag acacaaactt gatctttctg acctgtgtta
1141 cttctggacc ctctagctgt agctctccac gcctatgcag agacatctct atttctctct
1201 agttattggt gtttatttat tctttaccct tccacctcct cccctcccca gagacaccat
1261 gattcctggt aaccgaatgc tgatggtcgt tttattatgc caagtcctgc taggaggcgc
1321 gagccatgct agtttgatac ctgagacggg gaagaaaaaa gtcgccgaga ttcagggcca
1381 cgcgggagga cgccgctcag ggcagagcca tgagctcctt cgggacttcg aggccacact
1441 tctgcagatg ttcgggctgc gccgccgccc gcagcctagc aagagcgcag tcatcccgga
1501 ttacatgcgg gatctttaca gacttcagtc tggggaggag gaagaggaag agcagatcca
1561 gggcatcggt ctggagtatc ctgagcgccc cgccagtcgg gccaacaccg tgaggagctt
1621 ccaccacgaa ggtcagtccc ttacctggaa tctggactgg ggtggggcag tggaagctgt
1681 gggaaggcga ggagttcagg ttacatcaga gccccaaatc caggagactg ggaaaagaga
1741 gctgcttacc ttcaagagtc tccagagctg tggctgaatt tatttttggg agacagaagg
1801 gaagggaggg gtcggcgaga agggaatgac accactcaga cgtgggttag cccctgcggt
1861 gtgtttttgc tatatcaaag ccttttatgc caggttttct gccttttttt tttttttcca
1921 aagcacctac tgaatttaat attacagctg tgtgtttgtc aggtttattc aataggggcc
1981 ttgtaatccg atctgaatgt ttcctagcgg atgtttcttt tccaaagtaa atctgagtta
2041 ttaatccacc agcatcatta ctgtgttgga atttattttc ctctctgtaa catgatcaac
2101 aaggcatgct ctgtgtttcc aagatcgctg gggaaatgtt tggtaacata ctcgaaagtg
2161 gaagaagagg gagagggtgg ctgtgtgcat gttccctcct gcctctgctc tgttggcccc
2221 tcttcttctt tacaaccact tgtaaagaaa actgtgtaca caaagccaag agggctttaa
2281 aaggggagtc tgatggtggt ggagtaagga gttgacacat ggaaattatt agacatgtaa
  FORWARD PRIMER
2341 aggaggttgg gagattctgt ctttggtgct tgctgaatgc tagctaggct tggctggtct
2401 gctcactgcc tcatttatct gctctgtgaa attaaaggta tgcttatttc tcccaaatag
2461 gcttccacta taaacagagt tcactactca tcacccaact cttagctgtt tcttgacttt
2521 tcagtctctg aaaaagctca tttgcttttt ttctctgttc tcttattttt tttcctcccc
2581 aatggtgcct agaacatctg gagaacatcc cagggaccag cgaaaactct gcttttcgtt
2641 tcctctttaa cctcagcagc atcccagaga acgaggtgat ctcgtctgcc gagcttcgac
2701 t C/A ttccggga gcaggtggac cagggccctg actgggatca gggctttcat cgtataaaca
2761 tttatgaggt tatgaagccc ccggcagaag tggtgcctgg gcacctcatc acacgactac
```

Figure 3 Partial Sequence of Bovine BMP4 Gene

```
2821 tggacacaag actggtccac cacaatgtga cgcggtggga aacttttgat gtgagccctg
2881 cagtccttcg ctggacccgg gagaagcagc ccaactatgg gctggccatt gaggtgaccc
  REVERSE PRIMER
2941 acctccatca gacacggacc caccagggcc agcatgtcag gattagccga tcgttacctc
3001 aagggagtgg ggattgggcc cagctccggc ccctcctggt cacctttggc catgatggcc
3061 ggggacatgc cttgacccga cgcaggaggg ccaagcgtag ccccaagcat cacccacaga
3121 gggcccggaa gaagaataag aactgccggc gccactcgct ctacgtggac ttcagtgatg
3181 tgggctggaa tgactggatt gtggccccac caggctacca ggcattctac tgccacgggg
3241 actgcccctt tccactggcc gaccacctca actcaaccaa ccacgccatt gtgcagaccc
3301 tggtcaactc tgtcaattcc agtatcccca aagcctgttg tgttcccacc gaactcagcg
3361 ccatctccat gctgtacctg gatgagtatg acaaggtggt tctgaaaaat tatcaggaga
3421 tggtagtgga gggatgtggg tgccgctgag atcaggcctt ctttggggac acacacacac
3481 acacacacac acacacacac acacacacat cccatccact actcacccac acactacaca
3541 gactgcttcc ttatagctgg acttttatct taaaaaaaaa aaaaaggaaa aaaaaatcta
3601 aacattcacc ttgaccttat ttatgacttt acgtgcaaat gttttgacca tattgatcat
3661 atattttgac aaaatatatt tataactaca tattaaaaga aaaaaataaa atgagtcatt
3721 attttaaagg taaa
```

Figure 3 Partial Sequence of Bovine BMP4 Gene (continued)

GENETIC TESTING FOR IMPROVED CATTLE FERTILITY

CROSS REFERENCE TO RELATED APPLICATIONS

This is a divisional application of U.S. application Ser. No. 13/798,176 filed on Mar. 13, 2013 claiming priority to U.S. Patent Application No. 61/621,571 filed on Apr. 8, 2012, the entire disclosure of which is incorporated herein by reference.

STATEMENT OF GOVERNMENT INTEREST

This invention was made with government support under 12-CRHF-0-6055 awarded by the USDA/NIFA. The government has certain rights in the invention.

FIELD OF THE INVENTION

The present invention relates to methods for genetically testing cattle using molecular genetic methods by assaying for the presence of at least one genetic marker which is indicative of fertility. The present invention further relates to a method for assaying cattle embryo viability by assaying gene expression pattern in the embryo. Specifically, genetic variations in, and expression level of genes, of the transforming growth factor beta signaling pathway are tested for improved pre-implantation embryonic development in cattle.

BACKGROUND OF THE INVENTION

Dairy cows are significant investments for dairy farmers, and enormous efforts, such as animal breeding and artificial insemination, have been and continue to be made to ensure that the animals have high and sustained productivity, and that the milk produced is of high quality. The dairy cattle genome has been significantly restructured over the past 30 years due to intensive selection for production traits.

Reproductive deterioration in high-producing dairy cows has caused substantial economic loss in the dairy cattle industry (Lucy, 2007). Two of the key factors contributing to decreasing fertility of dairy cow are low fertilization rate and early embryonic mortality (Royal et al., 2000. Sheldon et al. 2006), both of which occur during the pre-implantation embryo development. Although genetic factors are known to affect reproductive performance (Shook, 2006), the identification of specific genes has been a challenge, probably due to the low accuracy of fertility data collected in the field, and the low heritability of these traits (VanRaden et al., 2004). Thus, understanding the genetic regulation of bovine pre-implantation embryo development and identifying associated biomarkers are becoming progressively essential to improving dairy cattle fertility.

To investigate the relationship between genetic factors and pre-implantation embryo development in bovine, the present inventor has created an in vitro fertilization (IVF) system, which enables the identification of genetic factors affecting fertilization and early embryonic development at both the cow and embryo levels. At the cow level, the IVF system has been utilized to uncover associations of cow genotypes with fertilization success and blastocyst rate of embryos produced from these cows (Driver et al. 2009; Huang et al. 2010a; Khatib et al. 2009a,b; Khatib et al. 2008a,b; Wang et al. 2009). At the embryo level, differential gene expression between normal blastocysts and degenerate embryos has been investigated by applying RNA-Seq (Huang & Khatib, 2010), microarray expression (Huang et al., 2010b), and candidate gene and pathway analyses (Laporta et al., 2011; Zhang et al., 2011).

The transforming growth factor-β (TGF-β) signaling pathway has long been acknowledged for signal transduction and other intracellular activities, such as cell division, differentiation, migration, apoptosis, and transformation (Santibanez et al., 2011). In addition, several studies have suggested the involvement of the TGF-β signaling cascade and its components in preimplantation embryo development as well as ovarian function (Shimasaki et al., 2004; Zhang et al., 2007). For example, Said et al. (2010) recently reported that known members of TGF-β pathway showed dynamic changes in gene expression profiles during the three early stages of human embryonic development, including oocytes, day-3 embryos, and human embryonic stem cells on day 7. Also, results from the mouse showed that multiple bone morphogenetic proteins (BMPs) and SMAD6 in the TGF-β pathway were found to be expressed in a stage-specific pattern and were developmentally regulated in oocytes and preimplantation embryos (Wang et al., 2004). BMPs and GDF9, also a member of TGF-β, have been reported as crucial regulators of folliculogenesis in mouse models (Otsuka et al. 2011; Trombly et al. 2009).

It is worth mentioning that most of the reported data on TGF-β pathway genes have been generated in the mouse model and there is little information on other species such as cattle. Interestingly, in a recent transcriptomic study of the bovine IVF system, the TGF-β pathway was found to be upregulated in degenerate embryos compared to blastocysts using microarrays (Huang et al., 2010b). However, several genes from this pathway were not included in the microarray analysis.

Many components of the signaling cascade of TGF-β pathway are known, and they include ligands (BMP4, GDF9, and INHBA); receptors (BMPR1A and ACVR1); SMAD proteins (SMAD2); upstream regulators (THBS2, THBS4, DCN); and downstream regulators (ID3, BMPER, PPP2R1A, RPS6KB2, PITX2). The signaling process of this pathway necessitates coordination of gene regulation among the different members of the pathway. For example, the activation of latent TGF-β requires binding of the thrombospondin-1 (THBS1) to the TGF-β precursor complex (Murphy-Ullrich & Poczatek, 2000). Protein phosphatase 2 (PPP2) and Ribosomal protein S6 kinase (RPS6K) are key regulators implicated in the phosphorylation of receptor and SMADs in the TGF-β signaling cascade (Fenton & Gout, 2010; Zolnierowicz, 2000). ID proteins are direct targets of BMP and TGF-β signaling, which serve as essential mediators in biological responses downstream the pathway (Miyazono & Miyazawa, 2002). The cell distribution and coordination of gene expression among the TGF-β genes testify to the significance of this pathway in embryo development.

Furthermore, the expression of many members of the TGF-β superfamily in the endometrium suggests a pivotal role of these genes in the differentiation of the endometrium and the implantation process (Jones et al. 2006). Consequently, the expression of TGF-β genes in preimplantation bovine embryos suggests an important role of these genes in the embryo-uterus connection. Indeed, it has been reported that blastocysts express TGF-β proteins that induce apoptosis of endometrial epithelial cells during implantation (Jones et al. 2006). Collectively, expression of TGF-β signaling genes in the bovine embryo suggests important role for the TGF-β pathway in the preimplantation stage of bovine embryo.

There are also reports that these genes function in maintaining pluripotency in the inner cell mass of bovine blastocysts (Pant & Keefer, 2009). Koide et al. (2009) demonstrated that overactivity of BMP4 signaling led to excessive apoptosis in early mammalian embryo development. Also, La Rosa et al. (2011) reported that supplementation of BMP4 to culture medium of IVF embryos decreased blastocyst production and concluded that a balanced BMP signaling activity is required for proper preimplantation development of cattle embryos.

The ID proteins function as key regulators of development by stimulating and maintaining proliferation and to preventing premature differentiation (Yokota & Mori, 2002), and are known to be regulated by other members of the TGF-β pathway such as BMPs (Hogg et al. 2010). BMPER is a BMP binding endothelial regulator and has been reported to modulate BMP4 signaling in endothelial cell differentiation and angiogenesis (Heinke et al. 2008; Moser et al. 2003).

Although the specific roles in bovine embryo development of differentially expressed genes are unknown, they have critical functions in the TGF-β signaling. For example, SMAD2 belongs to the SMAD family of proteins, which are transducers of TGF-β signal from the cell surface to the nucleus and transcription factors mediating the expression of target genes in the TGF-β cascade (Heldin et al. 1997; Massague et al. 2005). SMAD proteins are required for pluripotency maintenance of the inner cell mass in mouse blastocysts (James et al. 2005).

In a genome-wide association study, a SNP associated with fertilization rate was located within 50 Kb distance of ID3 (Huang et al. 2010a). Although the molecular regulation of fertilization success is not fully understood, maternal genome activity and oocyte quality appear to have critical roles in embryogenesis (Marteil et al. 2009; Stitzel & Seydoux, 2007). Recently, Hogg et al. (2010) observed that four ID isoforms (ID1-4) were expressed across the ovine ovarian follicle development and possibly regulated by TGF-β signaling via SMADs, and suggested mechanistic roles of the ID proteins in mammalian oocyte development. Furthermore, ID proteins are key regulators for many cellular processes, such as cell proliferation, differentiation, and cell cycle progression, which in turn are required for oocyte maturation, oocyte-to-embryo transition, and embryogenesis (Norton, 2000; Stitzel & Seydoux, 2007).

Indeed, it has been acknowledged that blastocyst yield can be affected by intrinsic oocyte quality (Rizos et al. 2002), and the involvement of BMP4 in ovarian function has been extensively reported (Shimasaki et al. 1999). The spatiotemporal expression of BMP4 signaling in follicle development has been broadly observed across different species including human, rat, bovine, swine, and zebrafish (Fatehi et al. 2005; Li & Ge, 2011; Nilsson & Skinner, 2003; Shimizu et al. 2004; Tanwar & McFarlane, 2011). Functional studies have also shown that BMP4 suppresses bovine granulose cell apoptosis and promotes follicle survival and development in rats (Kayamori et al. 2009; Nilsson & Skinner, 2003).

Nevertheless, even though the TGF-β signaling pathway was known to play a crucial role in ovarian and embryonic development, it had not been established whether the balance of expression level of various genes from this pathway is needed for proper preimplantation development of IVF embryos. Furthermore, there was limited information on the extent of contributions of maternal and embryonic genomes to the survival of the developing embryo. More importantly, no indication existed that variations of the maternal genotype in regard to the TGF-β genes had an impact on fertility rates. Identifying genetic factors that show association with fertility would enable selection or breeding programs that reduce the frequency of deleterious alleles at these loci by marker- or gene-assisted selection, preventing further decline or even improving reproductive status of the global dairy herd. In this regard, a plurality of or multiple genes are likely more reliable than a single gene or SNP in predicting high fertility or enhanced embryo survival.

SUMMARY OF THE INVENTION

The present inventor investigated the expression profiles of TGF-β genes in degenerate embryos and normal blastocysts and evaluated the association between maternal genotypes of the TGF-β genes and fertility traits, specifically fertilization success and blastocyst rate, and whether altered expression of TGF-β genes in preimplantation bovine embryos is associated with morphological abnormalities of these embryos, and concluded that TGF-β pathway genes play a vital function in the regulation of preimplantation embryo development at both embryo and cow levels, and that these genes can be used as genetic markers for embryo development and fertility in cattle.

Specifically, cattle embryos were produced and classified at the blastocyst stage as either normally-developed blastocysts or degenerates (growth-arrested embryos). The expression patterns of 25 genes from the TGF-β pathway were assessed using quantitative real time PCR. Ten genes showed differential expression between the two embryo groups, four genes displayed similar expressional profiles, and eleven genes had no detectable expression. An altered expression profile was found to be statistically significant for 10 out of the 14 expressed genes, and all were upregulated in degenerate embryos versus blastocysts.

Furthermore, genomic association analysis of the cows from which embryos were produced revealed a significant association of polymorphisms in DNA-binding protein inhibitor 3 (ID3) and bone morphogenetic protein 4 (BMP4)—two of the gens that showed the most significant differential expression—with fertilization rate and blastocyst rate, respectively.

Accordingly, in one embodiment, the present invention provides method for screening cattle embryos for implanting, the method comprising measuring the expression level of at least one Target Gene, without adversely affecting or at least maintaining the viability of the embryo, and selecting an embryo whose Target Gene expression level is not elevated for planting into a suitable uterus for further development. The Target Gene as used herein is a gene from the TGF-β pathway, preferably a gene selected from the group consisting of: DNA-binding protein inhibitor 3 (ID3); thrombospondin-2 (THBS2); bone morphogenetic protein 4 (BMP4); growth differentiation factor-9 (GDF9); BMP binding endothelial regulator (BMPER); decorin (DCN); SMAD family member 2 (SMAD2); thrombospondin-4 (THBS4); protein phosphatase 2, regulatory subunit A, alpha (PPP2R1A); and ribosomal protein S6 kinase, 70 kDa, polypeptide 2 (RPS6KB2).

In one embodiment, the expression level if the target gene is measured, e.g. via quantitative PCR, as a relative value against one or more housekeeping genes. In another embodiment, the expression level of the Target Gene(s) from a sample of a number of embryos, and those embryos whose gene expression level is higher than the others in the same sample are deemed to have up-regulated Target Gene expression and will be discarded. In another embodiment, the expression levels of a plurality of the Target Genes are measured against a plurality of housekeeping genes, to determine if the Target Genes are up-regulated or not. Because the Target Genes belong to the same signaling pathway, upregulation of one is indicative of upregulation of many or all in the same pathway, and is sufficient as an indication that the embryo is undesirable as an implant candidate.

In another embodiment, the present invention provides an isolated oligo- or polynucleotide molecule consisting of position 1213 of SEQ ID NO: 1, which represents a portion of the ID3 gene, and between 11 and 150 contiguous nucleotides adjacent to position 1213 of SEQ ID NO: 1, wherein position 1213 is cytosine or thymine. In addition, the present invention provides an isolated oligonucleotide molecule consisting of position 2702 of SEQ ID NO: 2, which represents a portion of the BMP4 gene, and between 11 and 150 contiguous nucleotides adjacent to position 2702 of SEQ ID NO: 2, wherein position 2702 is cytosine or adenine. Such isolated oligo- or polynucleotides are suitable for use as probes or primers for genotyping purposes, as are detailed elsewhere in this disclosure.

In one embodiment, the nucleotide molecule of the present invention comprises at least about 15 contiguous nucleotides adjacent to position 1213 of SEQ ID NO:1, or about 15 contiguous nucleotides adjacent to position 2702 of SEQ ID NO: 2. In one embodiment, the nucleic acid molecule of the present invention comprises at least about 20 contiguous nucleotides adjacent to the respective SNP positions (i.e. position 1213 of SEQ ID NO:1, or position 2702 of SEQ ID NO: 2). In one embodiment, the oligonucleotide molecule of the present invention consists of not more than about 100 nucleotides. In one embodiment, the oligonucleotide molecule of the present invention consists of not more than about 50 nucleotides. In one embodiment, the SNP position of the nucleotide molecule of the present invention near or at the center of the molecule; alternatively, the SNP position is at the 3'-end of the oligonucleotide molecule.

Also provided herein is an array of nucleic acid molecules comprising the isolated oligonucleotide molecule of the present invention, supported on a substrate. The substrate may be any suitable medium such as glass, known and readily available to one of ordinary skills in the art, and the array may be addressable.

The present invention further provides a kit comprising an isolated oligonucleotide molecule of the present invention, and a suitable container.

In another embodiment, the present invention provides a method for detecting single nucleotide polymorphism (SNP) in a gene encoding the DNA binding protein inhibitor 3 (ID3 gene), in a bovine cell, the method comprising determining the identity of a nucleotide on the ID3 gene of the cell at a position corresponding to position 1213 of SEQ ID NO: 1, and comparing the identity to the nucleotide identity at a corresponding position of in SEQ ID NO: 1.

The present invention further provides a method for detecting single nucleotide polymorphism (SNP) in a gene encoding the bone morphogenetic protein 4 (BMP4 gene) in a bovine cell, the method comprising determining the identity of a nucleotide on the BMP4 gene of the cell at a position corresponding to position 2702 of SEQ ID NO: 2, and comparing the identity to the nucleotide identity at a corresponding position of in SEQ ID NO: 2.

In one embodiment, the bovine cell may be an adult cell, an embryo cell, a sperm, an egg, a fertilized egg, or a zygote. The identity of the nucleotide may be determined by many methods known and readily available to those ordinarily skilled in the art, such as but not limited to sequencing a nucleic acid molecule comprising a suitable portion of the ID3 or BMP4 gene of the cell comprising respectively a position corresponding to position 1213 of SEQ ID NO: 1 or position 2702 of SEQ ID NO: 2; or by hybridizing a suitable probe to a nucleic acid preparation from the cell, which probe may be suitably labeled e.g. fluorescently or radioactively.

The nucleic acid molecule may be isolated from the cell via a large variety of methods, known and readily available to an ordinarily skilled artisan, such amplification by the polymerase chain reaction (PCR) of genomic DNA of the cell, or when appropriate, by RT-PCR of the mRNA of the cell.

In preferred embodiment, both copies of the gene in a diploid genome are genotyped according to the method of the present invention.

The identity of the nucleotide may be determined based on genotypes of the parent of the cell, genotypes of the daughter of the cell, or both, through genetic analysis methods well-known to those skilled in the art.

A method is further provided for determining whether an individual bovine animal is suitable as a gamete donor for natural mating, artificial insemination or in vitro fertilization, the method comprising detecting the SNP according to the above method of the present invention, and excluding as gamete donor an individual whose genotype is TT at a position in the ID3 gene corresponding to position 1213 of SEQ ID NO: 1. In one embodiment, the individual is excluded as a gamete donor if the individual, when mated with another parent, produces an offspring (e.g. a zygote or fertilized egg) whose genotype is TT at a position in the ID3 gene corresponding to position 1213 of SEQ ID NO: 1.

The present invention also provides a method for determining whether an individual bovine animal is suitable as a gamete donor for natural mating, artificial insemination or in vitro fertilization, the method comprising detecting the SNP according to the above method of the present invention, and selecting as a gamete donor an individual whose genotype is TT at a position in the BMP4 gene corresponding to position 2702 of SEQ ID NO: 2. In one embodiment, the individual is selected as a gamete donor if the individual, when mated with another parent, produces an offspring (e.g. a zygote or fertilized egg) whose genotype is TT at a position in the BMP4 gene corresponding to position 2702 of SEQ ID NO: 2.

The present invention additionally provides a method of selecting a bovine embryo for planting in a uterus, the method comprising genotyping the embryo according to the present invention, while preserving the viability of the embryo, and excluding from planting an embryo whose genotype is TT at a position in the ID3 gene corresponding to position 1213 of SEQ ID NO: 1, or selecting for planting an embryo whose genotype is TT at a position in the BMP4 gene corresponding to position 2702 of SEQ ID NO: 2.

In another embodiment, the present invention further provides a method for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo, and terminating pregnancy if the genotype of the developing embryo is TT at a position in the ID3 gene corresponding to position 1213 of SEQ ID NO: 1, or allowing pregnancy to proceed if the genotype of the embryo is TT at a position in the BMP4 gene corresponding to position 2702 of SEQ ID NO: 2. In one embodiment, the embryo is selected only if the genotype of the developing embryo is TT at a position in the BMP4 gene corresponding to position 2702 of SEQ ID NO: 2 but not TT at a position in the ID3 gene corresponding to position 1213 of SEQ ID NO: 1.

DESCRIPTION OF THE DRAWINGS

FIG. 2 shows the partial sequence of the ID3 gene (SEQ ID NO:1) where the relevant SNP position is noted, as well as the primers used for the qRT-PCR.

FIG. 3 shows the partial sequence of the BMP4 gene (SEQ ID NO:2) where the relevant SNP position is noted, as well as the primers used for the qRT-PCR.

DETAILED DESCRIPTION OF THE INVENTION

Figure 1:
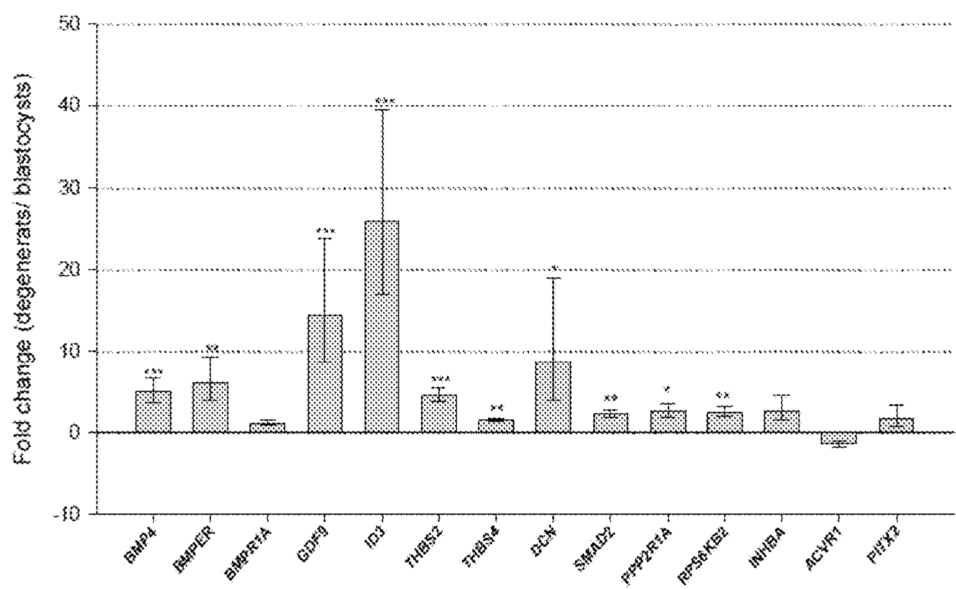
FIG. 1 shows differential expression, represented as fold change (Mean±SEM), of genes in the TGF-β pathway in degenerate embryos vs. blastocysts using qRT-PCR. Upregulation in degenerative embryos or blastocysts is shown by bars above or below the x-axis, respectively. The qRT-PCR was performed in three sets of biological replicates of blastocysts and degenerate embryos. * $p \leq 0.05$;  $p \leq 0.01$; * $p \leq 0.001$.

It has now been found that genes in the TGF-β pathway are involved in the development of preimplantation bovine embryos at both the embryonic and maternal levels. At the embryo level, some genes of the TGF-β pathway are upregulated in the growth-arrested embryos compared to normal blastocysts. At the maternal level, two genes are differentially-expressed in embryos, and their expression levels also show significant association with fertilization and blastocyst rates.

The expression profiles of the TGF-β genes in normally-developed blastocysts as compared to growth-arrested embryos produced from the same parents and cultured at the same laboratory conditions were examined, in order to investigate the role in blastocyst formation. It was found that fourteen (14) genes of the signaling cascade of TGF-β pathway were expressed in pre-implantation embryos, and these genes represent all components of the pathway, including ligands (BMP4, GDF9, and INHBA); receptors (BMPR1A and ACVR1); SMAD proteins (SMAD2); upstream regulators (THBS2, THBS4, DCN); and downstream regulators (ID3, BMPER, PPP2R1A, RPS6KB2, PITX2).

Out of the 14 expressed genes, 10 showed statistically significant expression differences between the embryo types, of which all were found to be upregulated in the degenerate embryos. Four genes that showed the most significant expression differences between embryo groups were tested for single nucleotide polymorphisms (SNP) association with fertilization and blastocyst rates, using an IVF experimental system that has been recently developed to identify genes affecting fertilization and embryo development in cattle. This IVF experimental system is fully described previously, e.g. in Driver et al. 2009; Huang et al. 2010a; Khatib et al. 2009a, 2009b; Khatib et al. 2008a, 2008b; Laporta et al. 2011; Wang et al. 2009, all of which are specifically incorporated herein by reference in their entirety.

A significant association was observed between ID3 maternal genotypes and fertilization rate. This result is consistent with a previous genome-wide association study, in which a SNP associated with fertilization rate was located within 50 Kb distance of ID3 (Huang et al. 2010a), and suggest that ID3 affects fertilization rate through maternal genome effects that control oocyte quality and oocyte-to-embryo transition.

Maternal genotypes of BMP4 were found to be significantly associated with blastocyst rate, suggesting its role in controlling intrinsic oocyte competence and development up to the blastocyst stage. The differential expression of BMP4 in embryos and the significant association of maternal genotypes with blastocyst rate indicate that this gene could regulate preimplantation embryo development not only through the embryo proper but also through the maternal genome.

More specifically, the present inventions identified two SNPs, one in the 3'untranslated region (3'UTR) of ID3, and one in the coding region (CDS) of BMP4. These SNPs were found to be in Hardy-Weinberg equilibrium (see Table 1). Estimates of the genotypic classes in each SNP for blastocyst and fertilization rate and relevant P values are given in Table 2 in the Examples. Analysis of SNP in ID3 revealed a significant association with fertilization rate ($P=0.029$). Oocytes from genotypes TT ovaries had 5.2% and 5.3% lower fertilization rates than those from TC and CC ovaries, respectively (Table 1). Blastocyst rate was significantly associated with SNP rs109778173 of BMP4 ($P=0.006$), whereas the association with fertilization rate was not statistically significant ($P=0.095$). Embryos produced from genotype TT cows showed 10.5% and 16.1% higher blastocyst rates than GG and GT cows, respectively (Table 2).

Accordingly, in one embodiment, the present invention provides a method for screening cattle embryos for implanting, the method comprising measuring the expression level of at least one Target Gene, while maintaining the viability of the embryo, and selecting an embryo whose Target Gene expression level is not elevated for planting into a suitable uterus for further development.

Methods of extracting a blastomere, or a single cell from a developing embryo, even at the early stage of development (5-8 cells), are readily known to those ordinarily skilled in the art, without affecting the viability of the embryo. Furthermore single cell cDNA analysis may be performed on the extracted blastomere, using methods well-established and readily available to those of ordinary skills in the art. See e.g. Amparo et al., Functional Genomics of 5- to 8-cell Stage Human Embryos by Blastomere Single-Cell cDNA Analysis, PLoS One 5(10) e13615, the entire content of which is incorporated herein by reference.

The Target Gene as used herein refers to a gene from the TGF-β pathway, preferably a gene selected from the group consisting of: DNA-binding protein inhibitor 3 (ID3); thrombospondin-2 (THBS2); bone morphogenetic protein 4 (BMP4); growth differentiation factor-9 (GDF9); BMP binding endothelial regulator (BMPER); decorin (DCN); SMAD family member 2 (SMAD2); thrombospondin-4 (THBS4); protein phosphatase 2, regulatory subunit A, alpha (PPP2R1A); and ribosomal protein S6 kinase, 70 kDa, polypeptide 2 (RPS6KB2).

In one embodiment, to determine whether the expression level of the target gene is up-regulated or not, the expression level of the Target Gene is measured as a relative value against one or more housekeeping genes. A housekeeping gene is typically a constitutive gene that is required for the maintenance of basic cellular function, and is expressed in all cells of an organism. Some housekeeping genes are expressed at relatively constant levels (such as HSP90 and Beta-actin), while other housekeeping genes may vary depending on experimental conditions, but are nevertheless suitable as internal control because the embryos or blastomere isolated therefrom are cultured under the same condition.

In another embodiment, the expression level of the Target Gene(s) from a sample of a number of embryos is measured. Generally, in a sample of sufficient size, the embryos will belong to two groups, one whose Target Gene expression level is higher than the other, and those embryos in the group of higher gene expression level are deemed to have up-regulated Target Gene expression and will be discarded according to the present invention. Statistically, and based on data obtained so far, it is reasonable to assume that in any given sample, e.g. of at least 10 embryos, some of the embryos will have a relatively low level of Target Gene expression while others will have a relatively high level. Because these embryos are cultured or otherwise treated under identical conditions, such relative upregulation, even without any other reference point or control, indicates that the Target Genes are up-regulated, and the embryos should be discarded. It is readily recognized that the larger the sample size, the more reliable the determination. Preferably, the number of embryos to be tested simultaneously should be at least 20 or higher.

In another embodiment, the expression levels of a plurality of the Target Genes are measured against a plurality of housekeeping genes, to determine if the Target Genes are up-regulated or not. This approach improves the reliability of the measurements, because the target genes belong to the same pathway, upregulation of one is indicative of upregulation of many or all, and is sufficient as an indication that the embryo is undesirable as an implant candidate.

It is readily recognized that the RNA should be extracted from the blastomere under conditions that provide a maximum representation of all transcribed RNA species present in the blastomere. The RNA should then be treated with a reverse transcription reaction mixture comprising a plurality of gene-specific oligonucleotides corresponding to at least a subset of said RNA species, dNTPs and a reverse transcriptase, under conditions allowing transcription of said RNA into complementary DNA (cDNA).

Furthermore, the present invention provides nucleic acid-based genetic markers for identifying bovine animals with superior fertility, specifically, fertilization or blastocyst rates. In general, for use as markers, isolated oligonucleotide or polynucleotide molecules, or isolated nucleic acid fragments, preferably DNA fragments, as used. Such markers will be of at least 10 nucleotides (nt), preferably at least 11, 12, or 15 nt, usually at least 20 nt, often at least 50 nt. Such small DNA fragments are useful as primers for the polymerase chain reaction (PCR), and probes for hybridization screening, etc.

In the context of the present invention, the term "isolated" refers to a nucleic acid molecule purified to some degree from endogenous materials with which the nucleic acid molecule may naturally occur or exist. At the least, the term "isolated" refers to a nucleic acid molecule separated from chromatin or other protein or components of the genomic DNA. Preferably, the isolated oligonucleic acid molecule or polynucleic acid molecule of the present invention comprises a fragment that is shorter than that which is naturally occurring.

The provided sequences also encompass the complementary sequence corresponding to any of the provided polymorphisms. Where appropriate, and in order to provide an unambiguous identification of the specific site of a polymorphism, the numbering of the original nucleic sequences in the GenBank may be used; alternatively, the numbering may simply refer to the specific sequence in the Sequence Listing accompanying this disclosure.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA or RNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified. One of these two primers is often referred to as the "forward primer," while the other the "reverse primer."

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or G. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the gene of interest. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the gene of the sample of interest may be amplified via PCR and directly sequenced, and the sequence be compared to the wild type sequence shown in the figures. It is readily recognized that, other than those disclosed specifically herein, numerous primers can be devised to achieve the objectives. PCR and sequencing techniques are well known in the art and reagents and equipments are readily available commercially.

Alternatively, an invasive signal amplification assay, as described in e.g. U.S. Pat. No. 5,422,253 and Lyamichev et al., 2000, Biochemistry 39:9523-9532, both incorporated herein by reference in their entirety, may be used for detecting the SNP of interest. This assay takes advantage of enzymes such as the 5' nuclease activity of a DNA polymerase or the gene 6 product from bacteriophage T7 in their ability to cleave polynucleotide molecules by recognizing specific structures instead of specific sequences. A single-stranded target molecule is annealed to a pilot oligonucleotide such that the 5' end of the pilot forms a duplex with the target molecule. If the 3' end of the pilot oligonucleotide does not pair with the target, a 3' arm is formed. When exposed to a cleavage agent such as a DNA polymerase having a 5' nuclease activity or the gene 6 product from bacteriophage T7, the target molecule is cleaved in the 5' region, one nucleotide into the duplex adjacent to the unpaired region of the target. If a cut in a double-stranded molecule is required, the double-stranded molecule is denatured. Because this unpaired 3' arm can be as short as one nucleotide, this assay can be used for detecting a single-nucleotide difference, e.g. in the context of SNP detection. The pilot oligonucleotide is designed such that it pairs perfectly with one allele, but has a 3', single nucleotide mismatch with another allele. Cleavage only occurs if there is a mismatch between the target molecule and the pilot. To achieve signal amplification, the above invasive reaction is modified such that cleavage occurs on the pilot oligonucleotide. Two oligonucleotides are annealed in an adjacent manner to the target molecule. The resulting adjacent duplexes overlaps by at least one nucleotide to create an efficient substrate, called the overlapping substrate, for the 5' nucleases. The 5' end of the downstream oligonucleotide, also called the probe, contains an unpaired region termed the 5' arm (Lyamichev et al., 1993, *Science* 260:778-783.) or flap (Harrington and Lieber, 1994, *EMBO J* 13: 1235-1246) that is not required for the enzyme activity; however, very long arms can inhibit cleavage (Lyamichev et al., 1993, *Science* 260:778-783). Specific cleavage of the probe, termed invasive cleavage (Lyamichev et al., 1999, *Nat. Biotechnol.* 17 292-296; Kwiatkowski et al., 1999, *Mol. Diagn.* 4, 353-364.), occurs at the position defined by the 3' end of the upstream oligonucleotide, which displaces or "invades" the probe. If the overlap between the adjacent oligonucleotides is only one nucleotide, cleavage takes place between the first two base pairs of the probe, thus releasing its 5' arm and one nucleotide of the base paired region (Lyamichev et al., 1999, *Proc. Natl. Acad. Sci. USA.* 96: 6143-6148, and Kaiser et al., 1999, *J Biol. Chem.* 274: 21387-21394). If the upstream oligonucleotide and the probe are present in large molar excess over the target nucleic acid, and invasive cleavage is carried out near the melting temperature of the probe, a cut probe can rapidly dissociate, and an intact probe will anneal to the target more frequently than will a cut probe, thus initiating a new cycle of cleavage. This allows multiple probes to be cut for each target molecule under isothermal conditions, resulting in linear signal amplification with respect to target concentration and time (Lyamichev et al., 1999, *Nat. Biotechnol.* 17: 292-296).

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved reproduction traits.

Further provided is a method for genotyping the bovine ID3 or BMP4 genes, comprising determining for the two copies of the gene in a diploid genome present the identity of the nucleotide pair at the relevant SNP position (see below).

One embodiment of a genotyping method of the invention involves examining both copies of the gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

In one embodiment, the present invention provides a method for selectively breeding of cattle, the method comprising selecting a suitable bovine animal having the desired genotype according to the method described above. In another embodiment, the present invention provides a cattle breeding method wherein a developing embryo is tested according to the genotyping method described above, and the embryo is allowed to develop further only if it has the desired genotype. In a further embodiment, a multiple ovulation and embryo transfer procedure (MOET) is used as part of the breeding procedure of the present invention, wherein the method comprises super-ovulating a female animal, collecting eggs from said superovulated female, in vitro fertilizing said eggs from a suitable male animal, implanting said fertilized eggs into other females allowing for an embryo to develop, and genotyping said developing embryo as described above, and terminating pregnancy if said developing embryo does not all have a desired genotype.

The method according to the present invention for determining whether an individual bovine animal is suitable as a gamete donor for natural mating, artificial insemination or in vitro fertilization, comprises detecting the SNP according to the above method of the present invention, and excluding as gamete donor an individual whose genotype is TT at a position in the ID3 gene corresponding to position 1213 of SEQ ID NO: 1; or detecting the SNP according to the above method of the present invention, and selecting as a gamete donor an individual whose genotype is TT at a position in the BMP4 gene corresponding to position 2702 of SEQ ID NO: 2.

In one embodiment, the individual is excluded as a gamete donor if the individual, when mated with another parent, produces an offspring (e.g. a zygote or fertilized egg) whose genotype is TT at a position in the ID3 gene corresponding to position 1213 of SEQ ID NO: 1. In one embodiment, the individual is selected as a gamete donor if the individual, when mated with another parent, produces an offspring (e.g. a zygote or fertilized egg) whose genotype is TT at a position in the BMP4 gene corresponding to position 2702 of SEQ ID NO: 2.

The present invention additionally provides a method of selecting a bovine embryo for planting in a uterus, the method comprising genotyping the embryo according to the present invention, while preserving the viability of the embryo, and excluding from planting an embryo whose genotype is TT at a position in the ID3 gene corresponding to position 1213 of SEQ ID NO: 1, or selecting for planting an embryo whose genotype is TT at a position in the BMP4 gene corresponding to position 2702 of SEQ ID NO: 2. In one embodiment, the embryo is selected only if the genotype of the developing embryo is TT at a position in the BMP4 gene corresponding to position 2702 of SEQ ID NO: 2 but not TT at a position in the ID3 gene corresponding to position 1213 of SEQ ID NO: 1.

In another embodiment, the present invention further provides a method for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo, and terminating pregnancy if the genotype of the developing embryo is TT at a position in the ID3 gene corresponding to position 1213 of SEQ ID NO: 1, or allowing pregnancy to proceed if the genotype of the embryo is TT at a position in the BMP4 gene corresponding to position 2702 of SEQ ID NO: 2. In one embodiment, the embryo is selected only if the genotype of the developing embryo is TT at a position in the BMP4 gene corresponding to position 2702 of SEQ ID NO: 2 but not TT at a position in the ID3 gene corresponding to position 1213 of SEQ ID NO: 1.

The following examples are intended to illustrate preferred embodiments of the invention and should not be interpreted to limit the scope of the invention as defined in the claims.

EXAMPLES

Materials and Methods

In this study, two different experiments were performed to assess the involvement of the TGF-β pathway genes in embryo development and fertility traits. In the first experiment, we compared the expression profiles of the TGF-β pathway genes in two populations of embryos differing in their morphology and development. The most significant differentially expressed genes between the embryo groups were tested in the second experiment for genomic association with fertility traits in a cow population.

I. Expression Profiles of TGF-β Pathway Genes in Cattle Embryos

Embryo Production and Morphological Classification

Oocytes were aspirated from ovaries obtained from a local slaughterhouse and underwent maturation until they were combined with frozen-thawed semen. The procedures of in vitro fertilization and subsequent embryo culture were as described in Khatib et al. (2008a,b). Embryos that showed signs of cellular compaction by Day 5 of culture (morula stage) were further cultured until Day 8. Embryos failing to show signs of compaction were excluded from further analysis. Embryos that exhibited a clear inner cell mass and a fluid filled cavity (blastocoele) on Day 8 were classified as blastocysts and those with abnormal blastocyst formation and morula-phenotype were classified as degenerates. Embryos randomly collected from each morphological group (n=20) were pooled and preserved in RNAlater (Ambion, Austin, Tex.). Three sets (blastocysts and degenerates) of embryo pools were used in the RNA expression analysis, in which two sets of biological replicate pools were produced from one sire and one set of embryos was produced from a second sire.

Real-time RT-PCR Quantification

Total RNA was extracted from pools of embryos using RNaqueous Micro (Ambion) and quality controlled by a RNA6000 PicoChip (Agilent Technologies, CA). The mRNA amplified by MessageAmp II (Ambion) was converted to cDNA using the iScript cDNA synthesis kit (Bio-Rad Laboratories, CA). Dilution of cDNA was used as template in qRT-PCR with the iQ SYBR Green Supermix kit (Bio-Rad Laboratories). The housekeeping gene glyceraldehyde-3-phosphate dehydrogenase (GAPDH) was selected as an endogenous control. Primers for 25 genes from the TGF-β pathway (Table 1) were designed to amplify fragments that span at least one intron to avoid genomic DNA contamination using the Beacon Designer software (Premier Biosoft International, Palo Alto, Calif.). Each sample was tested in quadruplicate. The relative quantification of gene expression was performed using 2-ΔΔct method (Livak & Schmittgen, 2001).

2 post-fertilization divided by the total number of fertilized oocytes collected from one ovary. Blastocyst rate was defined as the number of embryos that reached the blastocyst stage (Day 8) out of the total number of cultured embryos.

TABLE 1

Primers used for real-time RT-PCR, sequencing, and RFLP genotyping

| Gene | Forward primer 5'-3' | SEQ ID NO: | Reverse primer 5'-3' | SEQ ID NO: | Amplicon size(bp) |
|---|---|---|---|---|---|
| **Real time RT-PCR** | | | | | |
| ID3 | GCATCTTCCCATCCAGACA | 3 | CAGTGGCAGAAGCTCCTT | 4 | 75 |
| THBS2 | CTACTTCTCGGACCTCAA | 5 | TGGGTAACAGCATCTACA | 6 | 88 |
| THBS4 | GTGGGCTACATCAGGGTG | 7 | ATGGTGGTGTCTATGGTGA | 8 | 77 |
| PPP2R1A | CCTTCCTCTTGGTGGTTT | 9 | GGCCTTTATTTCTCTGTGAA | 10 | 85 |
| PITX2 | CCGCAGAGAAAGATAAGA | 11 | TTGCCTTTTCTTCTTGGA | 12 | 77 |
| BMP4 | TTTCCAGCAAGTTTGTTCA | 13 | CCATCAGCATTCGGTTAC | 14 | 106 |
| BMP3 | TGTCCTCACTCAGCATCT | 15 | GCAAGCACAAGACTCTACT | 16 | 89 |
| BMP2 | CACGAAGAATCTTTGGAAG | 17 | GTTCTGCTGAGGTGATAA | 18 | 109 |
| BMPER | GGACTACACTACTTTCTAC | 19 | GTATATGCCAGGAATGAT | 20 | 93 |
| BMPR1A | GTCTTACTCTGAACAAACAACT | 21 | GCTCTGATTCCTCCACTT | 22 | 125 |
| BMPR1B | CAGAACGGAATGAATGTAAT | 23 | AATGATGAGGACCAAGAG | 24 | 140 |
| SMAD2 | CCAACTCTTCTGTCATAG | 25 | GAACATAGGAAACCACTT | 26 | 126 |
| GDF9 | CCAAGACCATCCTGTGTA | 27 | CTTAGTGGCTATCATATCTTCATA | 28 | 108 |
| BMP15 | CCAAGAGGTAGTGAGGTT | 29 | AATACAGTAACAAGAAGACAGT | 30 | 76 |
| INHBA | GCAGAAATGAATGAACTTAT | 31 | CCTTCTTTGGAAATCTCA | 32 | 101 |
| DCN | CGATCATAAGTACATCCA | 33 | TCACTCCTGAATAAGAAG | 34 | 116 |
| RPS6KB2 | CATGGACAAGATCATCAGAG | 35 | CTGGTTAGGATTCCGCTT | 36 | 100 |
| SMAD1 | CCACTATAAGCGAGTAGAA | 37 | TGTGCTGAGGATTGTATT | 38 | 77 |
| SMAD6 | GTACAAGCCACTGGATCTATC | 39 | GCTGTGATGAGGGAGTTG | 40 | 75 |
| ACVR1 | GGATGAGAAGTCGTGGTT | 41 | TACTGGAGTGTCTTGATGTC | 42 | 110 |
| ACVR1C | AGTTCCGACCAAGTATTC | 43 | ACACTCACGCATTATTCT | 44 | 77 |
| ACVR1B | AGAGATATACCAGACAGT | 45 | GTGCCGTTATCTTTATTG | 46 | 78 |
| TGFβR1 | TTACCATTGCTTGTTCAG | 47 | CTTCTTCTCCTCTCCATT | 48 | 109 |
| TGFβR2 | TGTGTGGAAAGCATGAAGG | 49 | GATGCCCTGGTGGTTGAG | 50 | 84 |
| Lefty2 | AGCCAGAACTTCCGAGAG | 51 | CATGTCGAACACCAGCAA | 52 | 75 |
| GAPDH | TGCCCAGAATATCATCCC | 53 | AGGTCAGATCCACAACAG | 54 | 134 |
| **SNP identification** | | | | | |
| BMP4 (1) | GACCGCTGGAGGTTTGGG | 55 | GACTGAGGACTTTCCGTTTG | 56 | 637 |
| BMP4 (2) | TACAGGGCAATTCCTACTTT | 57 | GTCCAGATTCCAGGTAAGG | 58 | 628 |
| BMP4 (3) | TGGTGCTTGCTGAATGCT | 59 | GTGGGTCCGTGTCTGATG | 60 | 600 |
| BMP4 (4) | GGAGAAGCAGCCCAACTA | 61 | TCAGAACCACCTTGTCATAC | 62 | 506 |
| BMP4 (5) | GAGTATGACAAGGTGGTTCT | 63 | GAGTCTTTAATCCAGCCTA | 64 | 642 |
| ID3(1) | GCGGTATTCGGCGTCAGA | 65 | CGCACGGAGTTTGGAAGGT | 66 | 623 |
| ID3(2) | CTCCGTGCGTAAACCCTT | 67 | TTCCGTCATTCATTTGCTGT | 68 | 297 |
| ID3(3) | TCCGCCTGTGGTCTTTCG | 69 | CCTAAATCCAGCTTTGTGAGA | 70 | 733 |
| THBS2(1) | AACGAGTCCAGCTCTTCCG | 71 | TCCCTGCCTGCTTCAAAA | 72 | 322 |
| THBS2(2) | TCCGCTCCCGCACTTCAA | 73 | CCTCCCAGGAGTTTCCCACC | 74 | 416 |
| THBS2(3) | CAGTCTCCAAATTCTGTCCCTA | 75 | TGAGTTGACCCTTCTTTAT | 76 | 533 |
| THBS2(4) | CTGTTGCCAGTGACTTTA | 77 | CACATCATCATCCCGTAC | 78 | 527 |
| **SNP genotyping** | | | | | |
| BMP4 | TAGAACATCTGGAGAACATC | 79 | GGCTTCATAACCTCATAAATG | 80 | 190 |
| THBS2 | TCTTCACCTGCTGTCCTC | 81 | CTTACATTTCATATGTAAACCT | 82 | 206 |
| ID3 | TGGATGGGCCTCAACCTT | 83 | GGCAGAATTTGGAGAACAGC | 84 | 243 |

II. Association Study of TGF-β Pathway Genes with Fertilization and Blastocyst Rates To further evaluate the effects of the differentially expressed genes on fertility traits, maternal genotypes were tested for association with fertilization and blastocyst rates. The genes BMP4, THBS2, and ID3 were selected because they showed the most significant fold differences in expression between blastocysts and degenerates.

Phenotypic Data

Oocytes were collected from a total of 496 ovaries obtained from 496 Holstein cows and fertilized by semen samples from 12 Holstein bulls. For each cow, fertilization rate was defined as the number of cleaved embryos at Day 2 post-fertilization divided by the total number of fertilized oocytes collected from one ovary. Blastocyst rate was defined as the number of embryos that reached the blastocyst stage (Day 8) out of the total number of cultured embryos. A total of 7,865 fertilizations were performed and a total of 5,270 embryos were produced to generate fertilization and blastocyst rate data.

Polymorphism Identification and Genotyping

The DNA was isolated from ovaries (n=496) using standard phenol/chloroform protocols. DNA concentrations were measured using an Ultraspec 2100 spectrophotometer (Amersham Biosciences, Piscataway, N.J.). For single nucleotide polymorphism (SNP) identification, one DNA pool was constructed from 20 random ovary samples containing equal amounts of DNA from each (25 ng/μl). The DNA pool was amplified by 12 sets of primers designed from the exons of the three candidate genes (Table S1). Amplification, sequencing of PCR products, and SNP identification were as described in Khatib et al. (2008a, b). For genotyping, three sets of primers (Table S1) were designed in ID3, BMP4 and THBS2. The PCR products of SNP rs109818980 (ID3), rs109778173 (BMP4), and rs110619673 (THBS2) were digested with the restriction enzymes FauI, HinfI and TaiI, respectively and electrophoresed on a 2.0% agarose gel.

Statistical Analysis

For expression analysis, normalized gene expression values (ΔCt) were analyzed using a general linear model as follows:

$$y_{ijk}=\mu+b_i+p_j+\text{embryo}_{ijk}+e_{ijk} \quad (1)$$

where $y_{ijk}$ is the normalized gene expression value (ΔCt) of sample k from pool j fertilized by bull i; μ represents an overall mean for the trait considered; $p_j$ is the random effect of pool j; $b_i$ is the fixed effect of bull i; $\text{embryo}_{ijk}$ is the fixed effect of the embryo type; and $e_{ijk}$ represents the residual. Association between the normalized gene expression and the type of embryo was tested using a likelihood ratio test by comparing model (1) to a reduced model without the embryo effect. The mean and the range of the fold change for each gene were calculated as 2-ΔΔCt using the estimated ΔΔCt value±standard error. The analysis was performed by the LME4 package in R software.

The association of SNP genotypes with fertilization or blastocyst rate was tested using the following mixed linear model, $$y_{ijk}=\mu+o_i+b_i+SNP_{ijk}+e_{ijk} \quad (2)$$

where $y_{ijk}$ represents the fertilization rate or embryo survival rate of oocyte k from ovary i fertilized by bull j; μ represents an overall mean for the trait considered; $o_i$ is the random effect of the $i^{th}$ ovary from which oocytes were harvested; $b_i$ represents the random effect of the sire used in the fertilization; $SNP_{ijk}$ represents the fixed effect of the genotype for the SNP considered; and $e_{ijk}$ represents the residuals. Ovary and bull variables were assumed uncorrelated. Association between fertilization rate or embryo survival rate and SNP genotype was analyzed by the MIXED procedure of SAS (9.0).

Results

Two separate and complementary experiments were done in this study to investigate the roles of TGF-β genes in fertility traits in cattle. In the first experiment, we assessed and compared expression profiles of these genes in degenerate embryos that do not make a complete transition to blastocysts versus embryos that reach the blastocyst stage in a timely manner. In the second experiment, we tested the effects of the dams' genotypes on the fertilization and blastocyst rates of their embryos.

Differential Expression of the TGF-β Pathway Genes

A total of 25 genes from the TGF-β pathway were evaluated for their expression patterns in blastocysts and degenerate embryos; 14 genes were expressed and 11 genes were not detectable in embryos examined. FIG. 1 shows differential expression of the 14 expressed genes in embryos. Expression of all examined genes, except for ACVR1, was higher in degenerate embryos than blastocysts. The mRNA expression level of the following genes were significantly increased in degenerate embryos: DNA-binding protein inhibitor 3 (ID3; 25.8-fold difference: P<0.001), thrombospondin-2 (THBS2; 4.56-fold difference: P<0.001), bone morphogenetic protein 4 (BMP4; 4.96-fold difference; P=0.001), growth differentiation factor-9 (GDF9; 14.42-fold difference; P=0.001), BMP binding endothelial regulator (BMPER; 6.12-fold difference; P=0.004), and decorin (DCN; 8.57-fold difference; P=0.028). Moreover, lesser fold differences in expression, but still statistically significant, were observed for SMAD family member 2 (SMAD2; 2.26-fold difference; P=0.002), thrombospondin-4 (THBS4; 1.54-fold difference; P=0.006), protein phosphatase 2, regulatory subunit A, alpha (PPP2R1A; 2.56-fold difference; P=0.025) and ribosomal protein S6 kinase, 70 kDa, polypeptide 2 (RPS6KB2; 2.46-fold difference; P=0.007). However, the effect of embryo group was not statistically significant for the expression levels of BMP receptor, type 1A (BMPR1A), paired-like homeodomain 2 (PITX2), inhibin, beta A (INHBA) and activin A receptor, type1 (ACVR1) with fold change ranging from 1.16 to 2.64. Expression of BMP2, BMP3, BMP15, BMPR1B, SMAD1, SMAD6, TGF-βR2, TGF-βR1, ACVR1B, ACVR1C, and lefty2 was not detected in cattle embryos.

Association of Differentially Expressed Genes with Fertilization Rate and Blastocyst Rate Genes with the most significant differential expression between embryo types (ID3, GDF9, BMP4, and THBS2) were further investigated for association analysis of cow's genotype with fertilization and blastocyst rates. Using the pooled DNA sequencing method in the ovary/cow population, SNPs were identified in ID3, BMP4, and THBS2. No SNPs were detected in GDF9. The SNPs, rs109818980, rs109778173 and rs110619673, are located in the 3'untranslated region (3'UTR) of ID3, the coding region (CDS) of BMP4, and the 3' UTR of THBS2, respectively. SNPs were in Hardy-Weinberg equilibrium (Table 1). Estimates of the three genotypic classes in each SNP for blastocyst and fertilization rate and relevant P values are given in Table 1. Analysis of SNP rs109818980 in ID3 revealed a significant association with fertilization rate (P=0.029). Oocytes from genotypes TT ovaries had 5.2% and 5.3% lower fertilization rates than those from TC and CC ovaries, respectively (Table 1). Blastocyst rate was significantly associated with SNP rs109778173 of BMP4 (P=0.006), whereas the association with fertilization rate was not statistically significant (P=0.095). Embryos produced from genotype TT cows showed 10.5% and 16.1% higher blastocyst rates than GG and GT cows, respectively (Table 2). For SNP rs110619673 of THBS2, no significant associations were found with the examined traits (Table 2).

TABLE 2

P-values of HWE equilibrium test, estimate of blastocyst rate (±SE), and estimate of fertilization rate (±SE) for the ovary SNP genotypes in ID3, BMP4, and THBS2

| | | HWE | Blastocyst rate | | Fertilization rate | |
|---|---|---|---|---|---|---|
| Gene/SNP | Genotype[1] | P-value | Estimate ± SE | p-value | Estimate ± SE | P-value |
| ID3/rs109818980 | TT(237) | 0.089 | 0.338 ± 0.022 | 0.247 | 0.631 ± 0.028 | 0.029 |
| | TC(154) | | 0.304 ± 0.024 | | 0.683 ± 0.029 | |
| | CC(38) | | 0.371 ± 0.044 | | 0.684 ± 0.041 | |

TABLE 2-continued

P-values of HWE equilibrium test, estimate of blastocyst rate (±SE), and estimate of fertilization rate (±SE) for the ovary SNP genotypes in ID3, BMP4, and THBS2

| Gene/SNP | Genotype[1] | HWE P-value | Blastocyst rate Estimate ± SE | Blastocyst rate p-value | Fertilization rate Estimate ± SE | Fertilization rate P-value |
|---|---|---|---|---|---|---|
| BMP4/rs109778173 | GG(243) | 0.607 | 0.349 ± 0.019 | 0.006 | 0.675 ± 0.027 | 0.095 |
| | GT(162) | | 0.293 ± 0.022 | | 0.635 ± 0.028 | |
| | TT(23) | | 0.454 ± 0.053 | | 0.625 ± 0.046 | |
| THBS2/rs110619673 | CC(251) | 0.424 | 0.332 ± 0.022 | 0.371 | 0.652 ± 0.028 | 0.957 |
| | TC(147) | | 0.304 ± 0.026 | | 0.657 ± 0.030 | |
| | TT(26) | | 0.369 ± 0.054 | | 0.660 ± 0.046 | |

[1]in parenthesis is the number of cows genotyped

REFERENCES

Assou S, Boumela I, Haouzi D, Anahory T, Dechaud H, De Vos J & Hamamah S 2010. Dynamic changes in gene expression during human early embryo development: from fundamental aspects to clinical applications. *Human Reproduction Update* 17 272-290.

Driver A M, Huang W, Gajic S, Monson R L, Rosa G J & Khatib H 2009. Short communication: Effects of the progesterone receptor variants on fertility traits in cattle. Journal of Dairy Science 92 4082-4085.

Fatehi A N, van den Hurk R, Colenbrander B, Daemen A J, van Tol H T, Monteiro R M, Roelen B A & Bevers M M 2005. Expression of bone morphogenetic protein2 (BMP2), BMP4 and BMP receptors in the bovine ovary but absence of effects of BMP2 and BMP4 during IVM on bovine oocyte nuclear maturation and subsequent embryo development. *Theriogenology* 63 872-889.

Fenton T R & Gout I T 2010. Functions and regulation of the 70 kDa ribosomal S6 kinases. *International Journal of Biochemistry and Cell Biology* 43 47-59.

Heinke J, Wehofsits L, Zhou Q, Zoeller C, Baar K M, Helbing T, Laib A, Augustin H, Bode C, Patterson C & Moser M 2008. BMPER is an endothelial cell regulator and controls bone morphogenetic protein-4-dependent angiogenesis. *Circulation Research* 103 804-812.

Heldin C H, Miyazono K & ten Djke P 1997. TGF-beta signalling from cell membrane to nucleus through SMAD proteins. *Nature* 390 465-471.

Hogg K, Etherington S L, Young J M, McNeilly A S & Duncan W C 2010. Inhibitor of differentiation (Id) genes are expressed in the steroidogenic cells of the ovine ovary and are differentially regulated by members of the transforming growth factor-beta family. *Endocrinology* 151 1247-1256.

Huang W & Khatib H 2010. Comparison of transcriptomic landscapes of bovine embryos using RNA-Seq. *BMC Genomics* 11 711.

Huang W, Kirkpatrick B W, Rosa G J & Khatib H 2010a. A genome-wide association study using selective DNA pooling identifies candidate markers for fertility in Holstein cattle. *Animal Genetics* 41 570-578.

Huang W, Yandell B S & Khatib H 2010b. Transcriptomic profiling of bovine IVF embryos revealed candidate genes and pathways involved in early embryonic development. *BMC Genomics* 11 23.

James D, Levine A J, Besser D & Hemmati-Brivanlou A 2005. TGFbeta/activin/nodal signaling is necessary for the maintenance of pluripotency in human embryonic stem cells. *Development* 132 1273-1282.

Jones R L, Stolkos C, Findlay J K & Salamonsen L A 2006. TGF-beta superfamily expression and actions in the endometrium and placenta. *Reproduction* 132 217-232.

Kayamori T, Kosaka N, Miyamoto A and Shimizu T 2009. The differential pathways of bone morphogenetic protein (BMP)-4 and -7 in the suppression of the bovine granulosa cell apoptosis. *Molecular and Cellular Biochemistry* 323 161-168.

Khatib H, Huang W, Mikheil D, Schutzkus V & Monson R L 2009a. Effects of signal transducer and activator of transcription (STAT) genes STAT1 and STAT3 genotypic combinations on fertilization and embryonic survival rates in Holstein cattle. *Journal of Dairy Science* 92 6186-6191.

Khatib H, Huang W, Wang X, Tran A H, Bindrim A B, Schutzkus V, Monson R L & Yandell B S 2009b. Single gene and gene interaction effects on fertilization and embryonic survival rates in cattle. *Journal of Dairy Science* 92 2238-2247.

Khatib H, Maltecca C, Monson R L, Schutzkus V, Wang X & Rutledge J J 2008a. The fibroblast growth factor 2 gene is associated with embryonic mortality in cattle. *Journal of Animal Science* 86 2063-2067.

Khatib H, Monson R L, Schutzkus V, Kohl D M, Rosa G J & Rutledge J J 2008b. Mutations in the STAT5A gene are associated with embryonic survival and milk composition in cattle. *Journal of Dairy Science* 91 784-793.

Koide Y, Kiyota T, Tonganunt M, Pinkaew D, Liu Z, Kato Y, Hutadilok-Towatana N, Phongdara A & Fujise K 2009. Embryonic lethality of fortilin-null mutant mice by BMP-pathway overactivation. *Biochimica et Biophysica Acta* 1790 326-338.

Laporta J, Driver A & Khatib H 2011. Short communication: expression and alternative splicing of POU1F1 pathway genes in preimplantation bovine embryos. *Journal of Dairy Science* 94 4220-4223.

Li C W & Ge W 2011. Spatiotemporal expression of bone morphogenetic protein family ligands and receptors in the zebrafish ovary: a potential paracrine-signaling mechanism for oocyte-follicle cell communication. *Biology of Reproduction* 85 977-986.

Livak K J & Schmittgen T D 2001. Analysis of relative gene expression data using real-time quantitative PCR and the 2(-Delta Delta C(T)) Method. *Methods* 25 402-408.

Lucy M C 2007. Fertility in high-producing dairy cows: reasons for decline and corrective strategies for sustainable improvement. *Society of Reproduction and Fertility Supplement.* 64 237-254.

Martell G, Richard-Parpaillon L & Kubiak J Z 2009. Role of oocyte quality in meiotic maturation and embryonic development. *Reproductive Biology* 9 203-224.

Massague J, Seoane J & Wotton D 2005. Smad transcription factors. *Genes & Development* 19 2783-2810.

Miyazono K & Myazawa K 2002. Id: a target of BMP signaling. *Science's STKE* 151 pe40.

Moser M, Binder O, Wu Y, Altsebaomo J, Ren R, Bode C, Bautch V L, Conlon F L & Patterson C 2003. BMPER, a novel endothelial cell precursor-derived protein, antagonizes bone morphogenetic protein signaling and endothelial cell differentiation. *Molecular and Cellular Biology* 23 5664-5679.

Murphy-Ullrich J E & Poczatek M 2000. Activation of latent TGF-beta by thrombospondin-1: mechanisms and physiology. *Cytokine & Growth Factor Reviews* 11 59-69.

Nilsson E E & Skinner M K 2003. Bone morphogenetic protein-4 acts as an ovarian follicle survival factor and promotes primordial follicle development. *Biology of Reproduction* 69 1265-1272.

Norton J D 2000. ID helix-loop-helix proteins in cell growth, differentiation and tumorigenesis. *Journal of Cell Science* 113 3897-3905.

Otsuka F, McTavish K J & Shimasaki S 2011. Integral role of GDF-9 and BMP-15 in ovarian function. *Molecular Reproduction and Development* 78 9-21.

Pant D & Keefer C L 2009. Expression of pluripotency-related genes during bovine inner cell mass explant culture. *Cloning Stein Cells* 11 355-365.

Rizos D, Ward F, Duffy P, Boland M P & Lonergan P 2002. Consequences of bovine oocyte maturation, fertilization or early embryo development in vitro versus in vivo: implications for blastocyst yield and blastocyst quality. *Molecular Reproduction and Development* 61 234-248.

Rodriguez-Zas S L, Schellander K & Lewin H A 2008. Biological interpretations of transcriptomic profiles in mammalian oocytes and embryos. *Reproduction* 135 129-139.

Royal M, Mann G E & Flint A P 2000. Strategies for reversing the trend towards subfertility in dairy cattle. *The Veterinary Journal* 160 53-60.

Santibanez J F, Quintanilla M & Bernabeu C 2011. TGF-beta/TGF-beta receptor system and its role in physiological and pathological conditions. *Clinical Science* 121 233-251.

Sheldon I M, Wathes D C & Dobson H 2006. The management of bovine reproduction in elite herds. *The Veterinary Journal* 171 70-78.

Shimasaki S, Moore R K, Otsuka F & Erickson G F 2004. The bone morphogenetic protein system in mammalian reproduction. *Endocrine Reviews* 25 72-101.

Shimasaki S, Zachow R J, Li D, Kim H, lemura S, Ueno N, Sampath K, Chang R J & Erickson G F 1999. A functional bone morphogenetic protein system in the ovary. *Proceedings of the National Academy of Sciences of the United States of America* 96 7282-7287.

Shimizu T, Yokoo M, Miyake Y, Sasada H & Sato E 2004. Differential expression of bone morphogenetic protein 4-6 (BMP-4, -5, and -6) and growth differentiation factor-9 (GDF-9) during ovarian development in neonatal pigs. *Domestic Animal Endocrinology* 27 397-405.

Shook G E 2006. Major advances in determining appropriate selection goals. *Journal of Dairy Science* 89 1349-1361.

Stitzel M L & Seydoux G 2007. Regulation of the oocyte-to-zygote transition. *Science* 316 407-408.

Tanwar P S & McFarlane J R 2011. Dynamic expression of bone morphogenetic protein 4 in reproductive organs of female mice. *Reproduction* 142 573-579.

Trombly D J, Woodruff T K & Mayo K E 2009. Roles for transforming growth factor beta superfamily proteins in early folliculogenesis. *Seminars in Reproductive Medicine* 27 14-23.

VanRaden P M, Sanders A H, Tooker M E, Miller R H, Norman H D, Kuhn M T & Wiggans G R 2004. Development of a national genetic evaluation for cow fertility. *Journal of Dairy Science* 87 2285-2292.

Wang Q T, Piotrowska K, Ciemerych M A, Milenkovic L, Scott M P, Davis R W & Zernicka-Goetz M 2004. A genome-wide study of gene activity reveals developmental signaling pathways in the preimplantation mouse embryo. *Developmental Cell* 6 133-144.

Wang X, Schutzkus V, Huang W, Rosa G J & Khatib H 2009. Analysis of segregation distortion and association of the bovine FGF2 with fertilization rate and early embryonic survival. *Animal Genetics* 40 722-728.

Yokota Y & Mori S 2002. Role of Id family proteins in growth control. *Journal of Cellular Physiology* 190 21-28.

Zhang B, Penagaricano F, Driver A, Chen H & Khatib H 2011. Differential expression of heat shock protein genes and their splice variants in bovine preimplantation embryos. *Journal of Dairy Science* 94 4174-4182.

Zhang Y, Yang Z & Wu J 2007. Signaling pathways and preimplantation development of mammalian embryos. *The FEBS Journal* 274 4349-4359.

Zolnierowicz S 2000. Type 2A protein phosphatase, the complex regulator of numerous signaling pathways. *Biochemical Pharmacology* 60 1225-1235.

What is claimed is:

1. A method for selectively breeding a bovine animal, the method comprising detecting in a nucleic acid sample from a bovine animal a homozygous TT genotype in the bone morphogenetic protein 4 gene (BMP4 gene) at a position corresponding to position 2702 of SEQ ID NO: 2 and then breeding the bovine animal.

2. A method of selecting a bovine embryo for planting in a uterus, the method comprising detecting in a nucleic acid sample from the embryo a homozygous TT genotype in the bone morphogenetic protein 4 gene (BMP4 gene) at a position corresponding to position 2702 of SEQ ID NO: 2, and then planting the bovine embryo in a suitable uterus.

3. A method for selectively breeding a bovine animal using a multiple ovulation and embryo transfer procedure (MOET), the method comprising superovulating a female bovine animal, collecting eggs from said superovulated female animal, in vitro fertilizing said eggs with sperm from a suitable male animal, implanting said fertilized eggs into other females and allowing embryos to develop, detecting in a nucleic acid sample from an embryo a homozygous TT genotype in the bone morphogenetic protein 4 gene (BMP4 gene) at a position corresponding to position 2702 of SEQ ID NO: 2, and then allowing pregnancy to proceed.

4. A method for selectively breeding according to claim 1, wherein said breeding is by way of natural mating, artificial insemination or in virto fertilization.

* * * * *

SEQUENCE LISTING

```
<160> NUMBER OF SEQ ID NOS: 84

<210> SEQ ID NO 1
<211> LENGTH: 1700
<212> TYPE: DNA
<213> ORGANISM: Bos taurus
<220> FEATURE:
<221> NAME/KEY: misc_feature
<222> LOCATION: (1213)..(1213)
<223> OTHER INFORMATION: y is t or c

<400> SEQUENCE: 1

tctgtctatc tccttccttc cagcacttcc caacctcatt gctcagtatg aaggcgctca      60

gcccggttcg cggctgctac gaggcggtat gctgcctgtc ggaacgcagc ctggccatcg     120
```

```
cgcggggccg tggcaagagc ccggccgccg aggagccgct gagcctgctt gacgacatga    180

accactgcta ctcgcgactg agggaactgg tacccggagt cccgcgaggc actcagctta    240

gccaggtgga aatcctgcag cgcgtcatcg actacatcct cgacctgcag gtggtcctgg    300

ccgagccggc ccctgggccc ccagacggcc cgcatcttcc catccaggtg cgcgcgggcg    360

tgctcgggag ctggggcggg gctgagctcc agggctggga tgctacgggg acccctggac    420

cttccaaact ccgtgcgtaa acccttcccc cctttccttt ctctcagaca gctgagctcg    480

ctccggaact tgtgatctcc aacgaccaaa ggagcttctg ccactgacct ggcccgtcct    540

ggcgcctcca ggtgagtatc caagccttct ctcgggggcg gggaaggggg acagctggtg    600

cttaaacggc gatcttggag ttggtaggcc ttttaaagga ttaccgcggc cccctcggtt    660

tagggaaatt caggccagag agacgcaagt gacttgcccg tggtcacagc aaatgaatga    720

cggaaccaat tctgatccag agttcgtttc aaccttaagt gcacgttgtt cccgtcctcc    780

ccattggcca aaggtgcgaa actatagacg caggtccgac tagataaaat aaccagtctg    840

tctgtggctt ggagtcgtaa aaggagccgc gtttttctca gccccccctcc caactagtgt    900

cacttccaat aggcaggggt ggtgcaagct ccgcctgtgg tctttcggcg ccaactgggt    960

gggggcagtg tggggcgcga gttatcagct ggaggtagag accaagtttc ctccctggcg   1020

ccggccagtc tgcggacggc cccgcttggg gcgcgctcgg cggaaactga cggctccctg   1080

gtcttctttc ctcccccgcc cagaacgcag gtgctggcgc ccgtccggga ccccgggacc   1140

ctctacggcc ggaagcccga gggcatggat gggcctcaac cttgccctgc ccacttgact   1200

tccccaaacc ccygcctcga ggctggacct gcgcccggga gcgaaggact gtgaacttgg   1260

gtggcctaaa gagccggcgc tagctctggg caccagctgg gcaacctccc cctgccctca   1320

ccccactccc aagttttaaa gactgtcttt cagtgtgtgg aggtgtacgg ggttgggggt   1380

gggggctggc tgttctccaa attctgcctt ggccaaggca gcggtagagc tggtcttctg   1440

gtctccttgg agaaagactc tgttgccctg attatgaact ctataataga gtatttagct   1500

tttgtacctt ttttgcagga aggtgacttt ctgtaaccat gcgatgtata ttaaactttt   1560

tataaaagtt aacattttgc ataataaacg gtttttaaac acttgtgttt ataatttgat   1620

tccttaagtg ctaacactgt ttctcacaaa gctggattta gggagaataa attcatgtct   1680

ttcttggagc ttaggaaaag                                                1700
```

```
<210> SEQ ID NO 2
<211> LENGTH: 3734
<212> TYPE: DNA
<213> ORGANISM: Bos taurus
<220> FEATURE:
<221> NAME/KEY: misc_feature
<222> LOCATION: (2702)..(2702)
<223> OTHER INFORMATION: m is c or a 2702

<400> SEQUENCE: 2
```

```
aggggctgga agaaaaacag agtccgtctg cgccagtctc attatattca aatattcatt     60

ttaggagcca ttccgtagtg ccatccagag caacgcactg ccgcagctcc tctgagcctt    120

tccagcaagt ttgttcaaga ttggctgtca agaatcatgg actgttatta tatgccttgt    180

tttctgtcag tgagtagaca cctcttcctt ccctcttccc gggaattcac tctgccctcc    240

ccacccgcgc tcgccttgtg tccctcccgt cggaccttcc ttccagagtc cacactcttc    300

tttctggcag cgctgtcgct ttcttctagg ccgggcagcc actgcgctcg gagcctaccg    360

gttctggttg aagtgcagct tgctccactg gctctctgtc tgatcactgc gttacaagaa    420
```

```
aggggagcga gaaggggctg aacaaacgga aagtcctcag tcgggggagt tgaccgcccc    480
cctccccaca tgactgggag cacccagtgc ccctgtggcg cgctcctagc tgcttgtcaa    540
aactcacaga ggtcgccctt ggaatcatcc cctcccacac ccccttccct gggagtgagc    600
gagagggcgc gatcagatgc tttttgctgg gcatttcaaa actcctcagc cacagtaaaa    660
taaaccctct ggccactcgg tacgctccca gatcctgccg ccccgtgtct tcaccctgct    720
cctgcttctc tgctttccct ccctccgaac cagctggaag ttgtggaagt cgggctagga    780
agggcggagg aagaaggggg gtggaggaga agggagagag aggctgaagg tctgaagtgg    840
agaggagagc gctggcattt gaactctccc tcccccaccc ttctttacct tctcactgtt    900
aactgtttat ccctaaagaa gccaagctga gatcatggct cagatagcag ttgggacaaa    960
aaaagattaa caggatggag gctatctgat ttggggttat ttgactgtaa acaagttaga   1020
ccaagtaatt acagggcaat tcctactttc aggccgtgca tggctgcagc tggtggtggt   1080
ggtggggggg ggtgtgtgtg tcagaggaag acacaaactt gatctttctg acctgtgtta   1140
cttctggacc ctctagctgt agctctccac gcctatgcag agacatctct atttctctct   1200
agttattggt gtttatttat tctttaccct tccacctcct cccctcccca gagacaccat   1260
gattcctggt aaccgaatgc tgatggtcgt tttattatgc caagtcctgc taggaggcgc   1320
gagccatgct agtttgatac ctgagacggg gaagaaaaaa gtcgccgaga ttcagggcca   1380
cgcgggagga cgccgctcag ggcagagcca tgagctcctt cgggacttcg aggccacact   1440
tctgcagatg ttcgggctgc gccgccgccc gcagcctagc aagagcgcag tcatcccgga   1500
ttacatgcgg gatctttaca gacttcagtc tggggaggag gaagaggaag agcagatcca   1560
gggcatcggt ctggagtatc ctgagcgccc cgccagtcgg gccaacaccg tgaggagctt   1620
ccaccacgaa ggtcagtccc ttacctggaa tctggactgg ggtggggcag tggaagctgt   1680
gggaaggcga ggagttcagg ttacatcaga gccccaaatc caggagactg ggaaaagaga   1740
gctgcttacc ttcaagagtc tccagagctg tggctgaatt tattttttgg agacagaagg   1800
gaagggaggg gtcggcgaga agggaatgac accactcaga cgtgggttag cccctgcggt   1860
gtgtttttgc tatatcaaag ccttttatgc caggttttct gccttttttt ttttttttcca   1920
aagcacctac tgaatttaat attacagctg tgtgtttgtc aggtttattc aataggggcc   1980
ttgtaatccg atctgaatgt ttcctagcgg atgtttcttt tccaaagtaa atctgagtta   2040
ttaatccacc agcatcatta ctgtgttgga atttattttc ctctctgtaa catgatcaac   2100
aaggcatgct ctgtgtttcc aagatcgctg gggaaatgtt tggtaacata ctcgaaagtg   2160
gaagaagagg gagagggtgg ctgtgtgcat gttccctcct gcctctgctc tgttggcccc   2220
tcttcttctt tacaaccact tgtaaagaaa actgtgtaca caaagccaag agggctttaa   2280
aaggggagtc tgatggtggt ggagtaagga gttgacacat ggaaattatt agacatgtaa   2340
aggaggttgg gagattctgt ctttggtgct tgctgaatgc tagctaggct tggctggtct   2400
gctcactgcc tcatttatct gctctgtgaa attaaaggta tgcttatttc tcccaaatag   2460
gcttccacta taaacagagt tcactactca tcacccaact cttagctgtt tcttgacttt   2520
tcagtctctg aaaaagctca tttgcttttt ttctctgttc tcttattttt tttcctcccc   2580
aatggtgcct agaacatctg gagaacatcc cagggaccag cgaaaactct gcttttcgtt   2640
tcctctttaa cctcagcagc atcccagaga acgaggtgat ctcgtctgcc gagcttcgac   2700
tmttccggga gcaggtggac cagggccctg actgggatca gggctttcat cgtataaaca   2760
```

```
tttatgaggt tatgaagccc ccggcagaag tggtgcctgg gcacctcatc acacgactac   2820

tggacacaag actggtccac cacaatgtga cgcggtggga aacttttgat gtgagccctg   2880

cagtccttcg ctggacccgg gagaagcagc ccaactatgg gctggccatt gaggtgaccc   2940

acctccatca gacacggacc caccagggcc agcatgtcag gattagccga tcgttacctc   3000

aagggagtgg ggattgggcc cagctccggc ccctcctggt cacctttggc catgatggcc   3060

ggggacatgc cttgacccga cgcaggaggg ccaagcgtag ccccaagcat cacccacaga   3120

gggcccggaa gaagaataag aactgccggc gccactcgct ctacgtggac ttcagtgatg   3180

tgggctggaa tgactggatt gtggccccac caggctacca ggcattctac tgccacgggg   3240

actgcccctt tccactggcc gaccacctca actcaaccaa ccacgccatt gtgcagaccc   3300

tggtcaactc tgtcaattcc agtatcccca aagcctgttg tgttcccacc gaactcagcg   3360

ccatctccat gctgtacctg gatgagtatg acaaggtggt tctgaaaaat tatcaggaga   3420

tggtagtgga gggatgtggg tgccgctgag atcaggcctt ctttggggac acacacacac   3480

acacacacac acacacacac acacacacat cccatccact actcacccac acactacaca   3540

gactgcttcc ttatagctgg acttttatct taaaaaaaaa aaaaaggaaa aaaaaatcta   3600

aacattcacc ttgaccttat ttatgacttt acgtgcaaat gttttgacca tattgatcat   3660

atattttgac aaaatatatt tataactaca tattaaaaga aaaaaataaa atgagtcatt   3720

attttaaagg taaa                                                     3734
```

```
<210> SEQ ID NO 3
<211> LENGTH: 19
<212> TYPE: DNA
<213> ORGANISM: Artificial Sequence
<220> FEATURE:
<223> OTHER INFORMATION: Forward Primer ID3

<400> SEQUENCE: 3

gcatcttccc atccagaca                                                  19


<210> SEQ ID NO 4
<211> LENGTH: 18
<212> TYPE: DNA
<213> ORGANISM: Artificial Sequence
<220> FEATURE:
<223> OTHER INFORMATION: Reverse Primer ID3

<400> SEQUENCE: 4

cagtggcaga agctcctt                                                   18


<210> SEQ ID NO 5
<211> LENGTH: 18
<212> TYPE: DNA
<213> ORGANISM: Artificial Sequence
<220> FEATURE:
<223> OTHER INFORMATION: Forward Primer THBS2

<400> SEQUENCE: 5

ctacttctcg gacctcaa                                                   18


<210> SEQ ID NO 6
<211> LENGTH: 18
<212> TYPE: DNA
<213> ORGANISM: Artificial Sequence
<220> FEATURE:
<223> OTHER INFORMATION: Reverse Primer THBS2

<400> SEQUENCE: 6
```

```
tgggtaacag catctaca                                              18


<210> SEQ ID NO 7
<211> LENGTH: 18
<212> TYPE: DNA
<213> ORGANISM: Artificial Sequence
<220> FEATURE:
<223> OTHER INFORMATION: Forward Primer THBS4

<400> SEQUENCE: 7

gtgggctaca tcagggtg                                              18


<210> SEQ ID NO 8
<211> LENGTH: 19
<212> TYPE: DNA
<213> ORGANISM: Artificial Sequence
<220> FEATURE:
<223> OTHER INFORMATION: Reverse Primer THBS4

<400> SEQUENCE: 8

atggtggtgt ctatggtga                                             19


<210> SEQ ID NO 9
<211> LENGTH: 18
<212> TYPE: DNA
<213> ORGANISM: Artificial Sequence
<220> FEATURE:
<223> OTHER INFORMATION: Forward Primer PPP2R1A

<400> SEQUENCE: 9

ccttcctctt ggtggttt                                              18


<210> SEQ ID NO 10
<211> LENGTH: 20
<212> TYPE: DNA
<213> ORGANISM: Artificial Sequence
<220> FEATURE:
<223> OTHER INFORMATION: Reverse Primer PPP2R1A

<400> SEQUENCE: 10

ggcctttatt tctctgtgaa                                            20


<210> SEQ ID NO 11
<211> LENGTH: 18
<212> TYPE: DNA
<213> ORGANISM: Artificial Sequence
<220> FEATURE:
<223> OTHER INFORMATION: Forward Primer PITX2

<400> SEQUENCE: 11

ccgcagagaa agataaga                                              18


<210> SEQ ID NO 12
<211> LENGTH: 18
<212> TYPE: DNA
<213> ORGANISM: Artificial Sequence
<220> FEATURE:
<223> OTHER INFORMATION: Reverse Primer PITX2

<400> SEQUENCE: 12

ttgccttttc ttcttgga                                              18


<210> SEQ ID NO 13
<211> LENGTH: 19
<212> TYPE: DNA
```

<213> ORGANISM: Artificial Sequence
<220> FEATURE:
<223> OTHER INFORMATION: Forward Primer BMP4

<400> SEQUENCE: 13
tttccagcaa gtttgttca 19

<210> SEQ ID NO 14
<211> LENGTH: 18
<212> TYPE: DNA
<213> ORGANISM: Artificial Sequence
<220> FEATURE:
<223> OTHER INFORMATION: Reverse Primer BMP4

<400> SEQUENCE: 14
ccatcagcat tcggttac 18

<210> SEQ ID NO 15
<211> LENGTH: 18
<212> TYPE: DNA
<213> ORGANISM: Artificial Sequence
<220> FEATURE:
<223> OTHER INFORMATION: Forward Primer BMP3

<400> SEQUENCE: 15
tgtcctcact cagcatct 18

<210> SEQ ID NO 16
<211> LENGTH: 19
<212> TYPE: DNA
<213> ORGANISM: Artificial Sequence
<220> FEATURE:
<223> OTHER INFORMATION: Reverse Primer BMP3

<400> SEQUENCE: 16
gcaagcacaa gactctact 19

<210> SEQ ID NO 17
<211> LENGTH: 19
<212> TYPE: DNA
<213> ORGANISM: Artificial Sequence
<220> FEATURE:
<223> OTHER INFORMATION: Forward Primer BMP2

<400> SEQUENCE: 17
cacgaagaat ctttggaag 19

<210> SEQ ID NO 18
<211> LENGTH: 18
<212> TYPE: DNA
<213> ORGANISM: Artificial Sequence
<220> FEATURE:
<223> OTHER INFORMATION: Reverse Primer BMP2

<400> SEQUENCE: 18
gttctgctga ggtgataa 18

<210> SEQ ID NO 19
<211> LENGTH: 19
<212> TYPE: DNA
<213> ORGANISM: Artificial Sequence
<220> FEATURE:
<223> OTHER INFORMATION: Forward Primer BMPER

<400> SEQUENCE: 19
ggactacact actttctac 19

<210> SEQ ID NO 20
<211> LENGTH: 18
<212> TYPE: DNA
<213> ORGANISM: Artificial Sequence
<220> FEATURE:
<223> OTHER INFORMATION: Reverse Primer BMPER

<400> SEQUENCE: 20
gtatatgcca ggaatgat 18

<210> SEQ ID NO 21
<211> LENGTH: 22
<212> TYPE: DNA
<213> ORGANISM: Artificial Sequence
<220> FEATURE:
<223> OTHER INFORMATION: Forward Primer BMPR1A

<400> SEQUENCE: 21
gtcttactct gaacaaacaa ct 22

<210> SEQ ID NO 22
<211> LENGTH: 18
<212> TYPE: DNA
<213> ORGANISM: Artificial Sequence
<220> FEATURE:
<223> OTHER INFORMATION: Reverse Primer BMPR1A

<400> SEQUENCE: 22
gctctgattc ctccactt 18

<210> SEQ ID NO 23
<211> LENGTH: 20
<212> TYPE: DNA
<213> ORGANISM: Artificial Sequence
<220> FEATURE:
<223> OTHER INFORMATION: Forward Primer BMPR1B

<400> SEQUENCE: 23
cagaacggaa tgaatgtaat 20

<210> SEQ ID NO 24
<211> LENGTH: 18
<212> TYPE: DNA
<213> ORGANISM: Artificial Sequence
<220> FEATURE:
<223> OTHER INFORMATION: Reverse Primer BMPR1B

<400> SEQUENCE: 24
aatgatgagg accaagag 18

<210> SEQ ID NO 25
<211> LENGTH: 18
<212> TYPE: DNA
<213> ORGANISM: Artificial Sequence
<220> FEATURE:
<223> OTHER INFORMATION: Forward Primer SMAD2

<400> SEQUENCE: 25
ccaactcttc tgtcatag 18

<210> SEQ ID NO 26
<211> LENGTH: 18
<212> TYPE: DNA
<213> ORGANISM: Artificial Sequence
<220> FEATURE:

<223> OTHER INFORMATION: Reverse Primer SMAD2

<400> SEQUENCE: 26
gaacatagga aaccactt 18

<210> SEQ ID NO 27
<211> LENGTH: 18
<212> TYPE: DNA
<213> ORGANISM: Artificial Sequence
<220> FEATURE:
<223> OTHER INFORMATION: Forward Primer GDF9

<400> SEQUENCE: 27
ccaagaccat cctgtgta 18

<210> SEQ ID NO 28
<211> LENGTH: 24
<212> TYPE: DNA
<213> ORGANISM: Artificial Sequence
<220> FEATURE:
<223> OTHER INFORMATION: Reverse Primer GDF9

<400> SEQUENCE: 28
cttagtggct atcatatctt cata 24

<210> SEQ ID NO 29
<211> LENGTH: 18
<212> TYPE: DNA
<213> ORGANISM: Artificial Sequence
<220> FEATURE:
<223> OTHER INFORMATION: Forward Primer BMP15

<400> SEQUENCE: 29
ccaagaggta gtgaggtt 18

<210> SEQ ID NO 30
<211> LENGTH: 22
<212> TYPE: DNA
<213> ORGANISM: Artificial Sequence
<220> FEATURE:
<223> OTHER INFORMATION: Reverse Primer BMP15

<400> SEQUENCE: 30
aatacagtaa caagaagaca gt 22

<210> SEQ ID NO 31
<211> LENGTH: 20
<212> TYPE: DNA
<213> ORGANISM: Artificial Sequence
<220> FEATURE:
<223> OTHER INFORMATION: Forward Primer INHBA

<400> SEQUENCE: 31
gcagaaatga atgaacttat 20

<210> SEQ ID NO 32
<211> LENGTH: 18
<212> TYPE: DNA
<213> ORGANISM: Artificial Sequence
<220> FEATURE:
<223> OTHER INFORMATION: Reverse Primer INHBA

<400> SEQUENCE: 32
ccttctttgg aaatctca 18

<210> SEQ ID NO 33
<211> LENGTH: 18
<212> TYPE: DNA
<213> ORGANISM: Artificial Sequence
<220> FEATURE:
<223> OTHER INFORMATION: Forward Primer DCN

<400> SEQUENCE: 33
cgatcataag tacatcca 18

<210> SEQ ID NO 34
<211> LENGTH: 18
<212> TYPE: DNA
<213> ORGANISM: Artificial Sequence
<220> FEATURE:
<223> OTHER INFORMATION: Reverse Primer DCN

<400> SEQUENCE: 34
tcactcctga ataagaag 18

<210> SEQ ID NO 35
<211> LENGTH: 20
<212> TYPE: DNA
<213> ORGANISM: Artificial Sequence
<220> FEATURE:
<223> OTHER INFORMATION: Forward Primer RPS6KB2

<400> SEQUENCE: 35
catggacaag atcatcagag 20

<210> SEQ ID NO 36
<211> LENGTH: 18
<212> TYPE: DNA
<213> ORGANISM: Artificial Sequence
<220> FEATURE:
<223> OTHER INFORMATION: Reverse Primer RPS6KB2

<400> SEQUENCE: 36
ctggttagga ttccgctt 18

<210> SEQ ID NO 37
<211> LENGTH: 19
<212> TYPE: DNA
<213> ORGANISM: Artificial Sequence
<220> FEATURE:
<223> OTHER INFORMATION: Forward Primer SMAD1

<400> SEQUENCE: 37
ccactataag cgagtagaa 19

<210> SEQ ID NO 38
<211> LENGTH: 18
<212> TYPE: DNA
<213> ORGANISM: Artificial Sequence
<220> FEATURE:
<223> OTHER INFORMATION: Reverse Primer SMAD1

<400> SEQUENCE: 38
tgtgctgagg attgtatt 18

<210> SEQ ID NO 39
<211> LENGTH: 21
<212> TYPE: DNA
<213> ORGANISM: Artificial Sequence
<220> FEATURE:
<223> OTHER INFORMATION: Forward Primer SMAD6

<400> SEQUENCE: 39
gtacaagcca ctggatctat c 21

<210> SEQ ID NO 40
<211> LENGTH: 18
<212> TYPE: DNA
<213> ORGANISM: Artificial Sequence
<220> FEATURE:
<223> OTHER INFORMATION: Reverse Primer SMAD6

<400> SEQUENCE: 40
gctgtgatga gggagttg 18

<210> SEQ ID NO 41
<211> LENGTH: 18
<212> TYPE: DNA
<213> ORGANISM: Artificial Sequence
<220> FEATURE:
<223> OTHER INFORMATION: Forward Primer ACVR1

<400> SEQUENCE: 41
ggatgagaag tcgtggtt 18

<210> SEQ ID NO 42
<211> LENGTH: 20
<212> TYPE: DNA
<213> ORGANISM: Artificial Sequence
<220> FEATURE:
<223> OTHER INFORMATION: Reverse Primer ACVR1

<400> SEQUENCE: 42
tactggagtg tcttgatgtc 20

<210> SEQ ID NO 43
<211> LENGTH: 18
<212> TYPE: DNA
<213> ORGANISM: Artificial Sequence
<220> FEATURE:
<223> OTHER INFORMATION: Forward Primer ACVR1C

<400> SEQUENCE: 43
agttccgacc aagtattc 18

<210> SEQ ID NO 44
<211> LENGTH: 18
<212> TYPE: DNA
<213> ORGANISM: Artificial Sequence
<220> FEATURE:
<223> OTHER INFORMATION: Reverse Primer ACVR1C

<400> SEQUENCE: 44
acactcacgc attattct 18

<210> SEQ ID NO 45
<211> LENGTH: 18
<212> TYPE: DNA
<213> ORGANISM: Artificial Sequence
<220> FEATURE:
<223> OTHER INFORMATION: Forward Primer ACVR1B

<400> SEQUENCE: 45
agagatatac cagacagt 18

<210> SEQ ID NO 46
<211> LENGTH: 18

<212> TYPE: DNA
<213> ORGANISM: Artificial Sequence
<220> FEATURE:
<223> OTHER INFORMATION: Reverse Primer ACVR1B

<400> SEQUENCE: 46
gtgccgttat ctttattg 18

<210> SEQ ID NO 47
<211> LENGTH: 18
<212> TYPE: DNA
<213> ORGANISM: Artificial Sequence
<220> FEATURE:
<223> OTHER INFORMATION: Forward Primer TGF?AR1

<400> SEQUENCE: 47
ttaccattgc ttgttcag 18

<210> SEQ ID NO 48
<211> LENGTH: 18
<212> TYPE: DNA
<213> ORGANISM: Artificial Sequence
<220> FEATURE:
<223> OTHER INFORMATION: Reverse Primer TGF?AR1

<400> SEQUENCE: 48
cttcttctcc tctccatt 18

<210> SEQ ID NO 49
<211> LENGTH: 19
<212> TYPE: DNA
<213> ORGANISM: Artificial Sequence
<220> FEATURE:
<223> OTHER INFORMATION: Forward Primer TGF?AR2

<400> SEQUENCE: 49
tgtgtggaaa gcatgaagg 19

<210> SEQ ID NO 50
<211> LENGTH: 18
<212> TYPE: DNA
<213> ORGANISM: Artificial Sequence
<220> FEATURE:
<223> OTHER INFORMATION: Reverse Primer TGF?AR2

<400> SEQUENCE: 50
gatgccctgg tggttgag 18

<210> SEQ ID NO 51
<211> LENGTH: 18
<212> TYPE: DNA
<213> ORGANISM: Artificial Sequence
<220> FEATURE:
<223> OTHER INFORMATION: Forward Primer Lefty2

<400> SEQUENCE: 51
agccagaact tccgagag 18

<210> SEQ ID NO 52
<211> LENGTH: 18
<212> TYPE: DNA
<213> ORGANISM: Artificial Sequence
<220> FEATURE:
<223> OTHER INFORMATION: Reverse Primer Lefty2

<400> SEQUENCE: 52
catgtcgaac accagcaa 18

<210> SEQ ID NO 53
<211> LENGTH: 18
<212> TYPE: DNA
<213> ORGANISM: Artificial Sequence
<220> FEATURE:
<223> OTHER INFORMATION: Forward Primer GAPDH

<400> SEQUENCE: 53
tgcccagaat atcatccc 18

<210> SEQ ID NO 54
<211> LENGTH: 18
<212> TYPE: DNA
<213> ORGANISM: Artificial Sequence
<220> FEATURE:
<223> OTHER INFORMATION: Reverse Primer GAPDH

<400> SEQUENCE: 54
aggtcagatc cacaacag 18

<210> SEQ ID NO 55
<211> LENGTH: 18
<212> TYPE: DNA
<213> ORGANISM: Artificial Sequence
<220> FEATURE:
<223> OTHER INFORMATION: Forward Primer BMP4 (1)

<400> SEQUENCE: 55
gaccgctgga ggtttggg 18

<210> SEQ ID NO 56
<211> LENGTH: 20
<212> TYPE: DNA
<213> ORGANISM: Artificial Sequence
<220> FEATURE:
<223> OTHER INFORMATION: Reverse Primer BMP4 (1)

<400> SEQUENCE: 56
gactgaggac tttccgtttg 20

<210> SEQ ID NO 57
<211> LENGTH: 20
<212> TYPE: DNA
<213> ORGANISM: Artificial Sequence
<220> FEATURE:
<223> OTHER INFORMATION: Forward Primer BMP4 (2)

<400> SEQUENCE: 57
tacagggcaa ttcctacttt 20

<210> SEQ ID NO 58
<211> LENGTH: 19
<212> TYPE: DNA
<213> ORGANISM: Artificial Sequence
<220> FEATURE:
<223> OTHER INFORMATION: Reverse Primer BMP4 (2)

<400> SEQUENCE: 58
gtccagattc caggtaagg 19

<210> SEQ ID NO 59
<211> LENGTH: 18
<212> TYPE: DNA
<213> ORGANISM: Artificial Sequence
<220> FEATURE:
<223> OTHER INFORMATION: Forward Primer BMP4 (3)

<400> SEQUENCE: 59
tggtgcttgc tgaatgct 18

<210> SEQ ID NO 60
<211> LENGTH: 18
<212> TYPE: DNA
<213> ORGANISM: Artificial Sequence
<220> FEATURE:
<223> OTHER INFORMATION: Reverse Primer BMP4 (3)

<400> SEQUENCE: 60
gtgggtccgt gtctgatg 18

<210> SEQ ID NO 61
<211> LENGTH: 18
<212> TYPE: DNA
<213> ORGANISM: Artificial Sequence
<220> FEATURE:
<223> OTHER INFORMATION: Forward Primer BMP4 (4)

<400> SEQUENCE: 61
ggagaagcag cccaacta 18

<210> SEQ ID NO 62
<211> LENGTH: 20
<212> TYPE: DNA
<213> ORGANISM: Artificial Sequence
<220> FEATURE:
<223> OTHER INFORMATION: Reverse Primer BMP4 (4)

<400> SEQUENCE: 62
tcagaaccac cttgtcatac 20

<210> SEQ ID NO 63
<211> LENGTH: 20
<212> TYPE: DNA
<213> ORGANISM: Artificial Sequence
<220> FEATURE:
<223> OTHER INFORMATION: Forward Primer BMP4 (5)

<400> SEQUENCE: 63
gagtatgaca aggtggttct 20

<210> SEQ ID NO 64
<211> LENGTH: 19
<212> TYPE: DNA
<213> ORGANISM: Artificial Sequence
<220> FEATURE:
<223> OTHER INFORMATION: Reverse Primer BMP4 (5)

<400> SEQUENCE: 64
gagtctttaa tccagccta 19

<210> SEQ ID NO 65
<211> LENGTH: 18
<212> TYPE: DNA
<213> ORGANISM: Artificial Sequence
<220> FEATURE:
<223> OTHER INFORMATION: Forward Primer ID3(1)

<400> SEQUENCE: 65
gcggtattcg gcgtcaga 18

<210> SEQ ID NO 66
<211> LENGTH: 19
<212> TYPE: DNA
<213> ORGANISM: Artificial Sequence
<220> FEATURE:
<223> OTHER INFORMATION: Reverse Primer ID3(1)

<400> SEQUENCE: 66
cgcacggagt ttggaaggt 19

<210> SEQ ID NO 67
<211> LENGTH: 18
<212> TYPE: DNA
<213> ORGANISM: Artificial Sequence
<220> FEATURE:
<223> OTHER INFORMATION: Forward Primer ID3(2)

<400> SEQUENCE: 67
ctccgtgcgt aaaccctt 18

<210> SEQ ID NO 68
<211> LENGTH: 20
<212> TYPE: DNA
<213> ORGANISM: Artificial Sequence
<220> FEATURE:
<223> OTHER INFORMATION: Reverse Primer ID3(2)

<400> SEQUENCE: 68
ttccgtcatt catttgctgt 20

<210> SEQ ID NO 69
<211> LENGTH: 18
<212> TYPE: DNA
<213> ORGANISM: Artificial Sequence
<220> FEATURE:
<223> OTHER INFORMATION: Forward Primer ID3(3)

<400> SEQUENCE: 69
tccgcctgtg gtctttcg 18

<210> SEQ ID NO 70
<211> LENGTH: 21
<212> TYPE: DNA
<213> ORGANISM: Artificial Sequence
<220> FEATURE:
<223> OTHER INFORMATION: Reverse Primer ID3(3)

<400> SEQUENCE: 70
cctaaatcca gctttgtgag a 21

<210> SEQ ID NO 71
<211> LENGTH: 19
<212> TYPE: DNA
<213> ORGANISM: Artificial Sequence
<220> FEATURE:
<223> OTHER INFORMATION: Forward Primer THBS2(1)

<400> SEQUENCE: 71
aacgagtcca gctcttccg 19

<210> SEQ ID NO 72
<211> LENGTH: 18
<212> TYPE: DNA
<213> ORGANISM: Artificial Sequence
<220> FEATURE:
<223> OTHER INFORMATION: Reverse Primer THBS2(1)

<400> SEQUENCE: 72
tccctgcctg cttcaaaa 18

<210> SEQ ID NO 73
<211> LENGTH: 18
<212> TYPE: DNA
<213> ORGANISM: Artificial Sequence
<220> FEATURE:
<223> OTHER INFORMATION: Forward Primer THBS2(2)

<400> SEQUENCE: 73
tccgctcccg cacttcaa 18

<210> SEQ ID NO 74
<211> LENGTH: 20
<212> TYPE: DNA
<213> ORGANISM: Artificial Sequence
<220> FEATURE:
<223> OTHER INFORMATION: Reverse Primer THBS2(2)

<400> SEQUENCE: 74
cctcccagga gtttcccacc 20

<210> SEQ ID NO 75
<211> LENGTH: 22
<212> TYPE: DNA
<213> ORGANISM: Artificial Sequence
<220> FEATURE:
<223> OTHER INFORMATION: Forward Primer THBS2(3)

<400> SEQUENCE: 75
cagtctccaa attctgtccc ta 22

<210> SEQ ID NO 76
<211> LENGTH: 19
<212> TYPE: DNA
<213> ORGANISM: Artificial Sequence
<220> FEATURE:
<223> OTHER INFORMATION: Reverse Primer THBS2(3)

<400> SEQUENCE: 76
tgagttgacc cttctttat 19

<210> SEQ ID NO 77
<211> LENGTH: 18
<212> TYPE: DNA
<213> ORGANISM: Artificial Sequence
<220> FEATURE:
<223> OTHER INFORMATION: Forward Primer THBS2(4)

<400> SEQUENCE: 77
ctgttgccag tgacttta 18

<210> SEQ ID NO 78
<211> LENGTH: 18
<212> TYPE: DNA
<213> ORGANISM: Artificial Sequence
<220> FEATURE:
<223> OTHER INFORMATION: Reverse Primer THBS2(4)

<400> SEQUENCE: 78
cacatcatca tcccgtac 18

<210> SEQ ID NO 79

-continued

```
<211> LENGTH: 20
<212> TYPE: DNA
<213> ORGANISM: Artificial Sequence
<220> FEATURE:
<223> OTHER INFORMATION: Forward Primer BMP4

<400> SEQUENCE: 79

tagaacatct ggagaacatc                                        20


<210> SEQ ID NO 80
<211> LENGTH: 21
<212> TYPE: DNA
<213> ORGANISM: Artificial Sequence
<220> FEATURE:
<223> OTHER INFORMATION: Reverse Primer BMP4

<400> SEQUENCE: 80

ggcttcataa cctcataaat g                                      21


<210> SEQ ID NO 81
<211> LENGTH: 18
<212> TYPE: DNA
<213> ORGANISM: Artificial Sequence
<220> FEATURE:
<223> OTHER INFORMATION: Forward Primer THBS2

<400> SEQUENCE: 81

tcttcacctg ctgtcctc                                          18


<210> SEQ ID NO 82
<211> LENGTH: 22
<212> TYPE: DNA
<213> ORGANISM: Artificial Sequence
<220> FEATURE:
<223> OTHER INFORMATION: Reverse Primer THBS2

<400> SEQUENCE: 82

cttacatttc atatgtaaac ct                                     22


<210> SEQ ID NO 83
<211> LENGTH: 18
<212> TYPE: DNA
<213> ORGANISM: Artificial Sequence
<220> FEATURE:
<223> OTHER INFORMATION: Forward Primer ID3

<400> SEQUENCE: 83

tggatgggcc tcaacctt                                          18


<210> SEQ ID NO 84
<211> LENGTH: 20
<212> TYPE: DNA
<213> ORGANISM: Artificial Sequence
<220> FEATURE:
<223> OTHER INFORMATION: Reverse Primer ID3

<400> SEQUENCE: 84

ggcagaattt ggagaacagc                                        20
```